(12) United States Patent
Marcus et al.

(10) Patent No.: US 10,190,977 B2
(45) Date of Patent: Jan. 29, 2019

(54) METHOD OF MEASUREMENT OF MULTILAYER STRUCTURES

(71) Applicant: Lumetrics, Inc., Rochester, NY (US)

(72) Inventors: Michael A. Marcus, Honeoye Falls, NY (US); Donald S. Gibson, West Henrietta, NY (US); Kyle J. Hadcock, Webster, NY (US); Filipp V. Ignatovich, Rochester, NY (US)

(73) Assignee: LUMETRICS, INC., Rochester, NY (US)

( * ) Notice: Subject to any disclaimer, the term of this patent is extended or adjusted under 35 U.S.C. 154(b) by 0 days.

(21) Appl. No.: 15/585,495

(22) Filed: May 3, 2017

(65) Prior Publication Data

US 2018/0321145 A1    Nov. 8, 2018

(51) Int. Cl.

| G01B 11/06 | (2006.01) |
|---|---|
| G01B 9/02 | (2006.01) |
| G01N 21/45 | (2006.01) |
| G02B 27/12 | (2006.01) |
| G02B 27/30 | (2006.01) |
| H01S 3/00 | (2006.01) |
| H01S 3/22 | (2006.01) |

(52) U.S. Cl.
CPC ......... *G01N 21/45* (2013.01); *G01B 9/02002* (2013.01); *G01B 11/06* (2013.01); *G01N 2201/06113* (2013.01); *G02B 27/126* (2013.01); *G02B 27/30* (2013.01); *H01S 3/005* (2013.01); *H01S 3/0071* (2013.01); *H01S 3/2222* (2013.01)

(58) Field of Classification Search
CPC ......... G01N 21/45; G01N 2201/06113; G01B 9/02002; G01B 11/06; G01B 27/126; G01B 27/30; H01S 3/005; H01S 3/0071; H01S 3/2222
See application file for complete search history.

(56) References Cited

U.S. PATENT DOCUMENTS

| 5,387,309 A | * | 2/1995 | Bobel | ............... | G01B 11/0675 |
|---|---|---|---|---|---|
| | | | | | 117/85 |
| 5,596,409 A | | 1/1997 | Marcus et al. | | |

(Continued)

OTHER PUBLICATIONS

Cannon, Robert William, "Automated Spectral Identification of Materials Using Spectral Identity Mapping" (2013) ETD Archive. Paper 76.1. EFS File Name: 20170728 15-585495-IDS_NPL_Cite1.

*Primary Examiner* — Dominic J Bologna
(74) *Attorney, Agent, or Firm* — John M. Hammond; Patent Innovations LLC

(57) ABSTRACT

A method of identifying the material and determining the physical thickness of each layer in a multilayer structure is disclosed. The method includes measuring the optical thickness of each of the layers of the multilayer object as a function of wavelength of a light source and calculating a normalized group index of refraction dispersion curve for each layer in the multilayer structure. The measured normalized group index of refraction dispersion curves for each of the layers is then compared to a reference data base of known materials and the material of each layer is identified. The physical thickness of each layer is then determined from the group index of refraction dispersion curve for the material in each layer and the measured optical thickness data. A method for determining the group index of refraction dispersion curve of a known material is also disclosed.

14 Claims, 13 Drawing Sheets

(56) References Cited

U.S. PATENT DOCUMENTS

| | | | |
|---|---|---|---|
| 6,122,042 | A | 9/2000 | Wunderman et al. |
| 6,724,487 | B2 | 4/2004 | Marcus et al. |
| 2001/0043327 | A1 | 11/2001 | Barney et al. |
| 2003/0227632 | A1* | 12/2003 | Marcus ............... G01B 11/303 356/497 |
| 2007/0100580 | A1* | 5/2007 | Marcus ............. G01B 11/0683 702/170 |
| 2014/0239181 | A1* | 8/2014 | Hattori ............... G01B 11/0625 250/339.08 |
| 2015/0032417 | A1 | 1/2015 | Zobel |
| 2016/0061720 | A1 | 3/2016 | Lambert et al. |

* cited by examiner

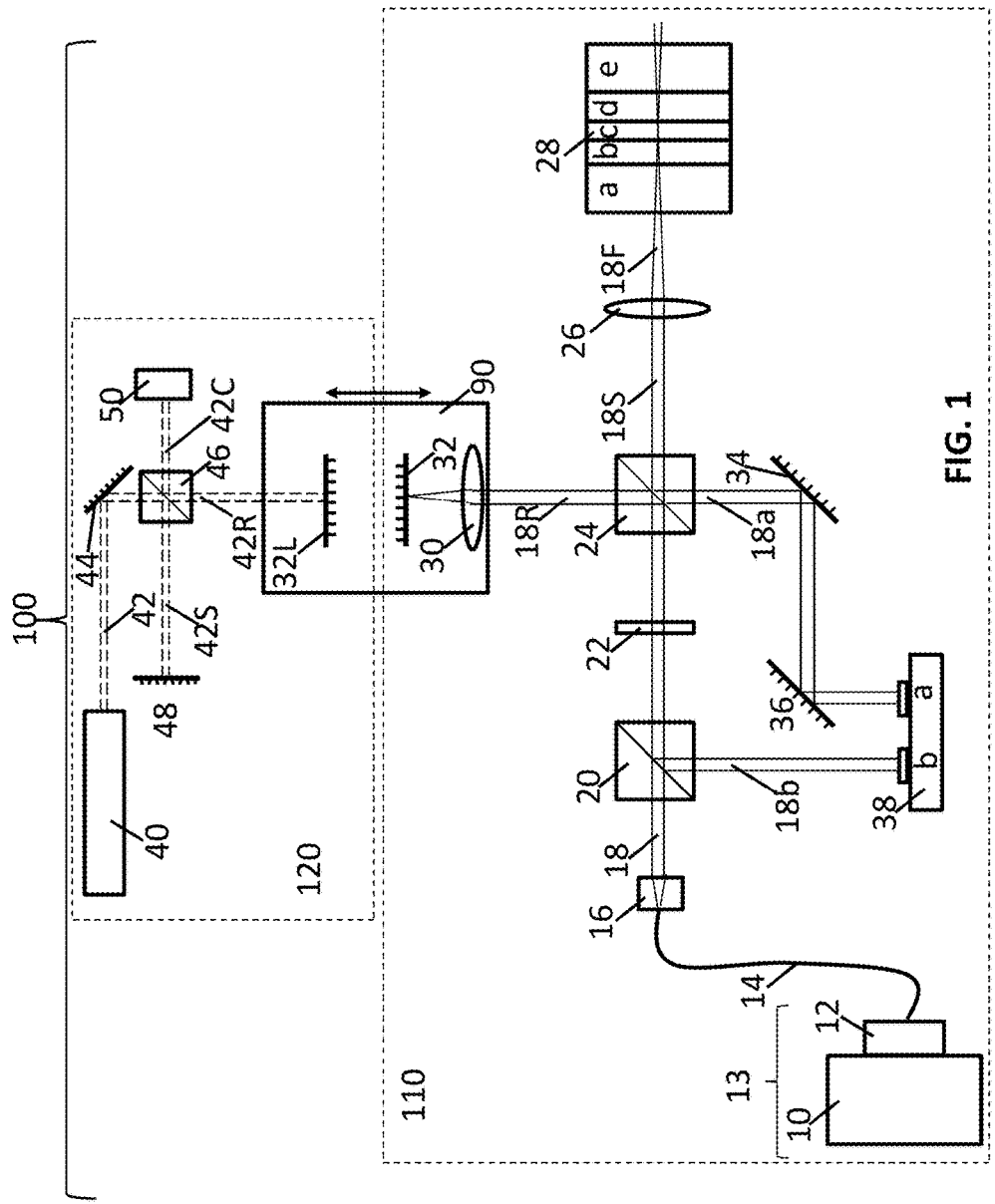

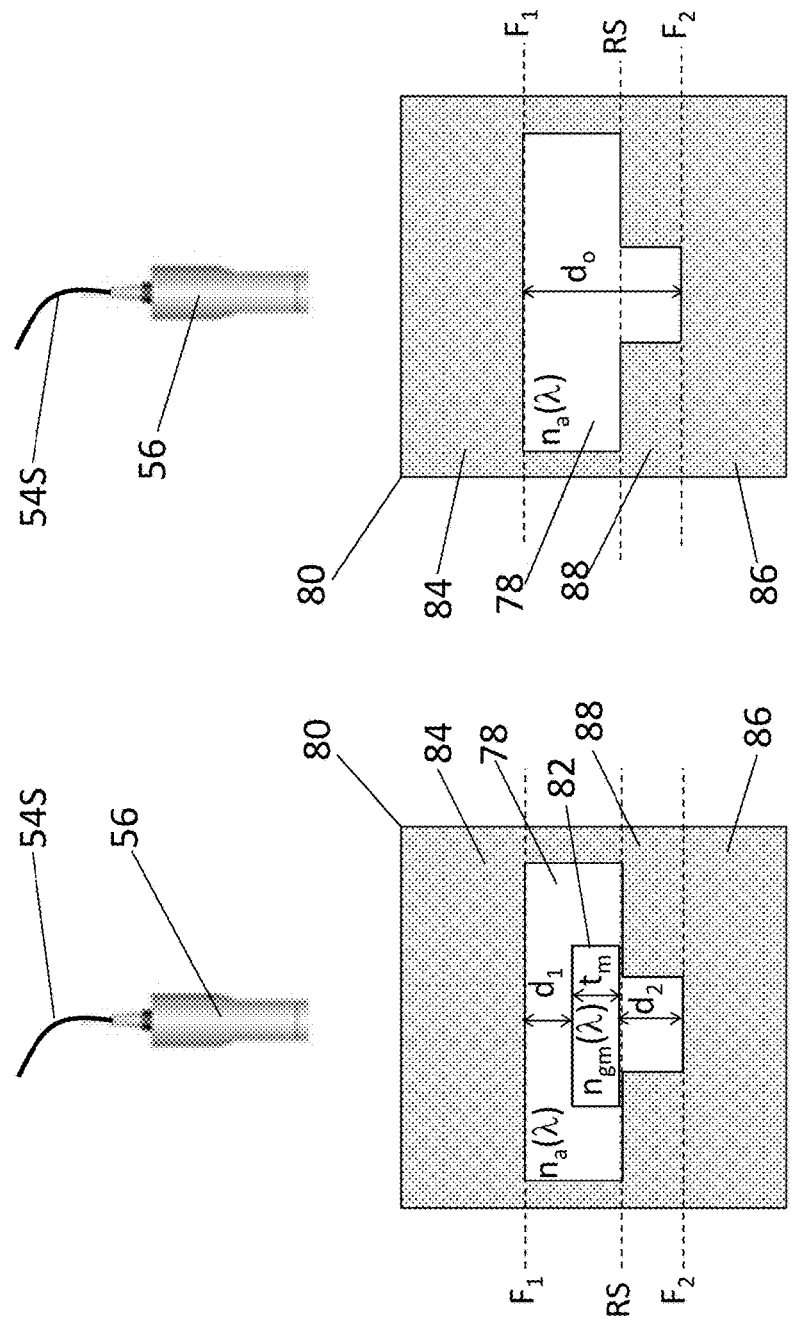

METHOD OF MEASUREMENT OF MULTILAYER STRUCTURES

BACKGROUND

Technical Field

The present invention relates to the non-destructive characterization of multilayer structures including determination of the number of layers, identification of the materials comprising each layer and the thickness of each layer in the multilayer structure.

Description of Related Art

Non-destructive product verification testing is important in many industries and is extremely important for multilayer structures used for a variety of commercial and military applications. Being able to identify the number of layers as well as the material that each layer is composed of in multilayer structures along with the thickness of each of the layers is becoming more and more important for product verification testing and is also useful in reverse engineering. It is extremely important to verify that the multilayer structures meet specifications in fields including automotive, aerospace and building glazing, transparent armor, compound lenses, semiconductors, displays, and bulletproof glass.

There are various methods of identifying single layer optical materials using the wavelength dependence of spectral properties including absorbance, reflectance, emission, scattering, fluorescence, Raman scattering, IR spectroscopy and index of refraction. As an example, the use of Raman spectroscopy is described in the master thesis entitled, "Automated Spectral Identification of Materials Using Spectral Identity Mapping" by Robert Cannon, May 2013. U.S. Pat. No. 6,122,042 entitled "Devices and Methods for Optically Identifying Characteristics of Material Objects" by Irwin Wunderman et al. describes a photometric analysis technique that collects scattered, reflected and emitted light. U.S. Patent Application Publication No. 2001/0043327 entitled "Spectral Identification System" by Bryan Barney et al. discloses the use of spectral reflectance over a broad spectral range from the ultra-violet (UV) to the near infra-red (NIR) to identify materials. U.S. Patent Application Publication No. 2016/0061720 entitled "Method for Characterizing a Product by Means of Topological Spectral Analysis" by Didier Lambert et al. describes a method of creating a data base of NIR data and using it to identify materials from their NIR spectra.

Optical dispersion in optical materials is the phenomenon in which the phase velocity of a wave depends on the wavelength of light λ traveling through the optical material. This results in a wavelength dependence of phase index of refraction which is different in different materials. An example of using optical dispersion to aid in material identification is provided by U.S. Patent Application Publication No. 2015/0032417 entitled "Systems and Methods for Identifying Optical Materials" by Jurgen Zobel ("Zobel '417" subsequently herein). Zobel '417 describes a method of material identification based on determining the index matching wavelength points for different index of refraction liquid standards. Zobel '417 uses the property of optical dispersion to identify the material in an optical material. In the measurement approach in Zobel '417 the index of refraction at is measured at three wavelengths by placing small grains of the material in different index matching fluids and determining which index matching fluid is the best fit at each of the three selected wavelengths. The temperature of the index of refraction liquid standards is also well characterized and the temperature that best matches the index of refraction of the material under test can also be found. However, the measurement procedure used in Zobel '417 is destructive since it requires the sample to be shattered into small grains and immersing it in the index matching liquids. It also can only measure one material at a time and is tedious.

Low-coherence interferometry (LCI) has applications in many fields from medical imaging to glass manufacturing. Low-coherence interferometry is based on using a light source with a relatively short coherence length on the order of 1.0-40 micrometers (μm). The light is split between two arms of an interferometer and then recombined and directed onto a detector. Interference will occur when the path lengths of the two arms of the interferometer are equal to within a few coherence lengths of the light source.

There are numerous known configurations of such interferometers, such as the Michelson, Mach-Zehnder, and Fizeau interferometers, and others described in the text, Principles of Optics: Electromagnetic Theory Of Propagation, Interference and Diffraction of Light, M. Born and E. Wolf, Cambridge University Press, Cambridge, N.Y., 1999, 7th ed. Other examples of such interferometer and described in U.S. Pat. No. 6,724,487 of Marcus et al., "Apparatus and method for measuring digital imager, package and wafer bow and deviation from flatness," and in U.S. Pat. No. 5,596,409 of Marcus et al., "Associated Dual Interferometric Measurement Method for Determining a Physical property of an Object", the disclosure of which are incorporated herein by reference ("Marcus '409" subsequently herein). The interferometer disclosed therein by Marcus '409 includes a low-coherence interferometer and a coherent light interferometer which are associated with each other by sharing a common variable optical path delay element. A narrow beam of low-coherence light is directed onto the surface of the test object. It is common to focus the beam inside or in proximity to the test object. The reflected light from all of the object interfaces, which the beam traverses, is then collected and analyzed by the interferometer. The interferometer is used to extract the optical distances between all of the optical interfaces in the test object. The physical distances are obtained by dividing the optical distances by the group index of refraction of the material which makes up the space between the interfaces. In a typical application, the light beam is directed along the optical axis of a lens. The axial thickness of the lens is then obtained by dividing the measured optical distance by the known group index of refraction of the glass or plastic material of the lens.

None of the above methods can both non-destructively determine the number of layers in a multilayer structure and identify the material used in each of the layers of the multilayer structure in the correct physical order of the materials in the structure. The disclosure of these patents and published patent applications notwithstanding, there remains an unmet need to be able to identify the material that each of the layers in a multilayer structure is composed of non-destructively. There also remains an unmet need to determine the thickness of each of the layers in the multilayer structure while identifying the material composition of each of the layers in the multilayer structure. Such a measurement method and system would be an important advance to the fields of non-destructive product verification testing and reverse engineering.

SUMMARY

In accordance with the present disclosure, the unmet need for a measurement system and method that enables non-destructive material identification of each of the layers in a multilayer structure is solved by providing an interferometer apparatus with a low-coherence tunable light source to determine the normalized group index of refraction of each of the layers in the multilayer structure as a function of wavelength. From the wavelength dependence of the normalized group index of refraction data, the material that each of the layers in the multilayer structure is composed of can be identified.

In a first embodiment of the invention a method of identifying the material composition of each layer in a multilayer structure comprising m layers where m is an integer greater than 1 is provided. The method comprises the steps of providing an interferometer apparatus with a low-coherence tunable light source and aligning a portion of the multilayer structure with respect to a measurement region of the interferometer apparatus and measuring the optical thickness of each of the observed layers in the multilayer structure as a function of center wavelength of the low-coherence tunable light source using the interferometer apparatus. The method also includes the steps of determining the number of layers m in the multilayer structure by setting m equal to the maximum number of observed layers measured using the low coherence interferometer as a function of center wavelength of the low-coherence tunable light source and calculating the normalized group index of refraction dispersion curves for each of the m layers in the multilayer structure by selecting one center wavelength of the tunable light source as a reference wavelength and calculating the ratio of the measured optical thickness at each measurement wavelength to that measured at the selected reference wavelength for each of the m layers in the multilayer structure. The method also includes the step of identifying the material for each of the m layers by comparing its calculated normalized group index of refraction dispersion curve to a reference data base of known materials group index of refraction dispersion curves and finding the best fit material for each of the m layers in the multilayer structure.

In a second embodiment of the invention, a method for determining the group index of refraction dispersion curve of a known material is provided. The method comprises the steps of providing a flat single layer sample of the known material, providing a measurement cell comprising a top flat having a bottom optically flat surface and a bottom optical flat having a top optically flat surface separated by a gap larger than the thickness of the flat single layer sample, the bottom and top optically flat surfaces being parallel to each other and providing an interferometer apparatus with a low-coherence tunable light source and an optical probe normally aligned with respect to the optically flat surfaces of the measurement cell. The method also comprises the steps of using the interferometer apparatus to determine the gap between the bottom optically flat surface of the top flat and the top optically flat surface of the bottom flat of the measurement cell and mounting the flat single layer sample of the known material in the measurement cell in the gap between the bottom optically flat surface of the top flat and the top optically flat surface of the bottom flat. The method further comprises the steps of using the interferometer apparatus to determine the top gap between the bottom optically flat surface of the top flat and the top surface of the known material sample, the optical thickness of the known material sample and the bottom gap between the bottom surface of the known material sample and the top optically flat surface of the bottom flat as a function of wavelength of the low-coherence tunable light source and calculating the physical thickness of the known material sample by subtracting the sum of the top gap and the bottom gap from the gap. The final step is then to determine the group index of refraction dispersion curve of the known material by dividing the optical thickness of the known material sample measured as a function of wavelength of the low-coherence tunable light source by the physical thickness of the known material sample.

These and other aspects, objects, features and advantages of the present invention will be more clearly understood and appreciated from a review of the following detailed description of the preferred embodiments and appended claims, and by reference to the accompanying drawings.

BRIEF DESCRIPTION OF THE DRAWINGS

The present disclosure will be provided with reference to the following drawings, in which like numerals refer to like elements, and in which:

FIG. 1 shows a schematic of a first embodiment of an interferometer apparatus used to measure the optical thickness of each of the layers in a multilayer structure as a function of wavelength.

FIG. 7A shows an embodiment of an index of refraction measurement cell used for measuring known materials and adding them to the group index of refraction dispersion curve data base including a known material sample present in a cavity thereof, and FIG. 7B shows the cell without the known material sample present in the cavity.

DETAILED DESCRIPTION

Figure 1A:
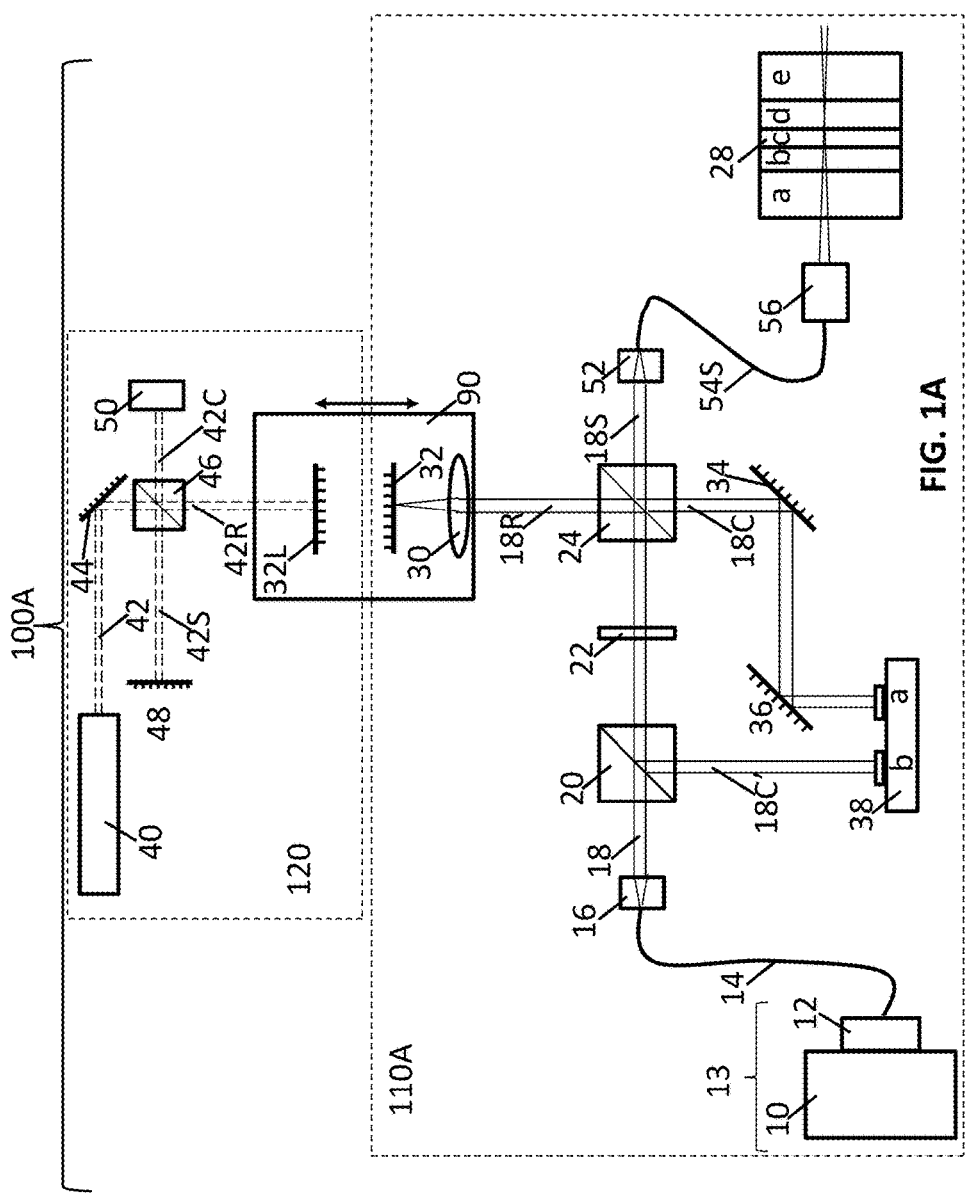
FIG. 1A shows a schematic of a second embodiment of an interferometer apparatus used to measure the optical thickness of each of the layers in a multilayer structure as a function of wavelength.

The present description is directed in particular to elements forming part of, or cooperating more directly with, apparatus in accordance to the invention. For a general understanding of the present invention, reference is made to the drawings. It is to be understood that elements not specifically shown or described may take various forms well known to those skilled in the art. In the following description and drawings, identical reference numerals have been used, where possible, to designate identical elements. Figures shown and described herein are provided in order to illustrate key principles of operation of the present invention and are not drawn with intent to show actual size or scale. Some exaggeration, i.e., variation in size or scale may be necessary in order to emphasize relative spatial relationships or principles of operation. One of ordinary skill in the art will be able to readily determine the specific size and interconnections of the elements of the example embodiments of the present invention.

In the following disclosure, the present invention is described in the context of a method to determine the number of layers in a multilayer structure and to identify the material comprising each layer of the multilayer structure and to measure the physical thickness of each of its layers. In the context of the present disclosure, a suitable multilayer structure is considered to be an object comprised of m layers where m is a positive integer greater than 1, each of the m layers being at least partially transparent to light over at least part of the optical spectrum and has an optical interface with each of its adjacent layers. The optical spectrum is defined as the portion of the electromagnetic spectrum ranging from the extreme ultraviolet through the far-infrared. When the term "multilayer structure" is used in the context of the present disclosure, it is to be understood that the multilayer structure is partially optically transmissive over at least part of the optical spectrum over which the measurement is performed. The multilayer structure is also required to have "nearly parallel" surfaces at the location of measurement. In the context of the present disclosure the term "nearly parallel" is defined to be parallel within ±3°. Each layer of the multilayer structure should also be 10 µm or greater in physical thickness. Example multilayer structures include automotive, aerospace and building glazing, transparent armor such as that found on tanks and armored vehicles, compound lenses, multilayer semiconductor wafers, displays and bulletproof glass.

Also throughout the present disclosure we use the term mirror which we define as a reflective surface or a partially reflective surface in which a negligible amount of light is transmitted. Furthermore, the terms refractive index and index of refraction can be used interchangeably.

Additionally, this description may identify certain components with the adjectives "top," "upper," "bottom," "lower," "left," "right," "horizontal," "vertical," "inner," "outer," "transmitted," "reflected," etc. These adjectives are provided in the context of use of the apparatus as a measurement device, and in the context of the orientation of the drawings, which is arbitrary. The description is not to be construed as limiting the apparatus to use in a particular spatial orientation. The instant apparatus may be used in orientations other than those shown and described herein. As an example in the disclosure we describe light beams incident on beam splitters which split the beam into transmitted and reflected light beams which then interact with different sets of components. It is to be understood that the orientation of the drawing can be altered so that the transmitted beam interacts with the components shown interacting with the reflected light beam and vice versa. When the beam splitter is used in an interferometer we call the two arms of the interferometer sample and reference arms.

The following description describes the details of our invention directed at identifying the material composition and physical thickness of each of the layers in a multilayer structure. In the practice of the invention an interferometer apparatus is used to first measure the optical thickness of each of the layers of a multilayer structure in order from top to bottom as a function of wavelength $\lambda$ of a tunable light source. Throughout the discussion of the invention all materials and multilayer structures are measured at the same set of k distinct center wavelengths of the tunable light source defined as $\lambda_j$ where j is an integer and j=1 to k inclusively with $\lambda_1$ being the shortest center wavelength of the tunable light source and $\lambda_k$ being the longest wavelength of the tunable light source. Each successive wavelength measured is at a longer wavelength than the previous one so that $\lambda_1 < \lambda_2 < \lambda_3 \ldots < \lambda_{k-1} < \lambda_k$.

In our context, the term "optical thickness of a layer" is defined as the product of the group index of refraction times the physical thickness $[n_{gi}(\lambda_j)t_i]$ where $n_{gi}(\lambda_j)$ is the group index of refraction of the ith layer in the multilayer structure measured at wavelength $\lambda_j$ and $t_i$ is the physical thickness of the ith layer. For a multilayer structure comprised of m layers, the individual layers will be sequentially labeled with integers numbered from 1-m from top to bottom of the multilayer structure. The optical thickness measured for each of the layers will vary with wavelength of the filtered light source due to changes in the group index of refraction as a function of wavelength. The variation in optical thickness as a function of wavelength is different for different materials. We determine the normalized group index of refraction curve for each layer in the multilayer structure and then compare the data to normalized group index of refraction dispersion curves found in a reference data base of known materials to identify the statistically best fit material for each of the layers in the multilayer structure. In the following disclosure, we first describe the instrument, and then describe how the optical dispersive properties measured can be used to identify the material that each of the layers in the multilayer structure is composed of and how to determine the physical thickness of each of the layers. We then describe how new materials can be added to the reference data base of known materials.

Turning now to FIG. 1, a schematic of a first embodiment of an interferometer apparatus 100 used to measure the optical thickness of each of the layers in a multilayer structure 28 as a function of wavelength is shown. The interferometer apparatus 100 is a dual interferometer comprising a free-space low-coherence interferometer 110 (shown in the lower dashed rectangle) and a laser interferometer 120 (shown in the upper dashed rectangle). The two interferometers share a common variable optical path delay element 90 as described in Marcus '409. The laser interferometer 120 continuously measures the displacement of the reference path and is used to provide an accurate distance scale for the low-coherence interferometer as described in Marcus '409.

As shown in FIG. 1, the light source of the free space low-coherence interferometer 110 is a broadband low-coherence light source 10, and preferably a supercontinuum light source such as an NKT Photonics EXW-12 Supercontinuum light source (SCLS) which emits light over the wavelength range of 400-2400 nanometers (nm). The light coming out of the broadband light source 10 is coupled into a continuously variable wavelength tunable filter 12. The broadband low-coherence light source 10 and the continuously variable wavelength tunable filter 12 together form a tunable light source 13. For many materials, the preferred continuously variable wavelength tunable filter is one that can be tuned anywhere between 400 and 850 nm with a bandwidth being variable between 5 and 50 nm such as an NKT Photonics SuperK VARIA tunable wavelength filter. For other materials which do not transmit light in the visible range, including semiconductors such as silicon and germanium, tunable filters in the range of 1100 nm-2400 nm or longer are preferred. The preferred bandwidth range of the tunable filter is between 5-20 nm in order to deliver a near Gaussian wavelength distribution of light into the low-coherence interferometer. Light exiting the tunable filter 12 is coupled into a single mode fiber 14 which is preferably a single mode photonic crystal fiber (PCF) since it will function properly over the entire wavelength range of the tunable filter 12. The light transmitted through the single mode fiber 14 is coupled into a fiber collimator 16 which forms a collimated beam 18 shown as a pair of parallel solid lines in FIG. 1. The collimated light beam 18 is passed through a polarizing beam splitter (PBS) 20 which linearly polarizes the transmitted collimated light beam. The transmitted collimated linearly polarized light beam then passes through a quarter wave plate (QWP) 22 and is input into a beam splitter (BS) 24 which forms a Michelson interferometer. The beam splitter 24, preferably a 50/50 beam splitter, splits the input collimated beam 18 into a sample arm collimated beam 18S and a reference arm collimated beam 18R that travel through the sample and reference arms of the Michelson interferometer respectively.

Both the sample arm collimated beam 18S and the reference arm collimated beam 18R are comprised of incident light and reflected light portions as described below. The incident light portion of sample arm collimated beam 18S originates from the beam splitter 24 and passes through sample arm lens 26 and is focused onto the multilayer structure 28 under test as shown by the focusing low coherence beam 18F. The focus region of the lens 26 defines the measurement region of the interferometer apparatus. Before measurement, the multilayer structure 28 is mounted in the measurement region of the low coherence interferometer 110 and aligned so that its top and bottom surfaces are close to normal (within ±3°) to the center axis of the incident low coherence beam 18F. The incident light portion of reference arm collimated beam 18R also originates from the beam splitter 24 and passes through reference arm lens 30 and is focused on the reference mirror 32. The sample and reference arm lenses 26 and 30 are preferably achromatic doublets or triplets in order to have the same focal length over the entire wavelength range of measurement.

The reference arm lens 30 and reference mirror 32 are co-mounted on a variable optical path delay element 90 as is laser reference mirror 32L. The variable optical path element is preferably a precision linear actuator, voice coil or translation stage which is moved during operation of the interferometer apparatus 100. Part of the light that is focused on the multilayer structure 28 through sample arm lens 26 reflects off each optical interface of the multilayer structure 28 and is recollimated by the sample arm lens 26 makes up the reflected light portion of sample arm collimated beam 18S. Similarly, the part of the incident light that is focused on the reference mirror 32 through the reference arm lens 30 and reflects off reference mirror 32 and is recollimated by the reference arm lens 30 makes up the reflected light portion of reference arm collimated beam 18R.

The multilayer structure shown in FIG. 1 is comprised of 5 layers 28a-28e and has 6 optical interfaces (air/28a, 28a/28b, 28b/28c, 28c/28d, 28d/28e and 28e/air). Light reflecting back from the reference mirror 32 and each of the optical interfaces in the multilayer structure 28 are re-collimated at their respective reference arm lens 30 and sample arm lens 26 to form the reflected light portions of the reference and sample arm collimated beams 18R and 18S respectively. The reflected light portions of the reference and sample arm collimated beams 18R and 18S are then recombined at the 50/50 beam splitter 24 to form a collimated low-coherence interference beam. After being recombined the collimated low-coherence interference beam is split again at the same beam splitter 24 into a transmitted low-coherence interference beam 18a and a reflected low-coherence interference beam 18b. The transmitted low-coherence interference beam 18a is incident on the first detector 38a of a balanced detector 38 after reflecting off a pair of 45° mirrors 34 and 36. The reflected low-coherence interference beam 18b travels back through the quarter wave plate 22 and is incident on the polarizing beam splitter 20 where it is reflected and is made to be incident on a second detector 38b of the balanced detector 38. The balanced detector 38 signal is filtered, log amplified and the envelope of the low-coherence interferometer signal is measured as a function of distance traveled by the variable optical path delay element 90 during measurement. Use of balanced detection results in an improved signal to noise ratio due to removal of common mode noise and enables the ability to use higher powers without saturating the detector.

FIG. 1A shows a schematic of a second embodiment of an interferometer apparatus 100A used to measure the optical thickness of each of the layers in a multilayer structure 28 as a function of wavelength. Most of the components of interferometer apparatus 100 and 100A are the same, and all components of the laser interferometer 120 are the same in both embodiments. The only differences in the components between low-coherence interferometer 110A and low-coherence interferometer 110 occur in the sample arm of the low-coherence interferometer 110A. The focusing lens 26 is replaced with a fiber collimator 52 which is used to couple the incident light portion of sample arm collimated beam 18S into a sample arm optical fiber 54S which is then input into an optical probe 56 which focuses light onto the multilayer structure 28. Part of the light that is focused on the multilayer structure 28 through optical probe 56 reflects off each optical interface of the multilayer structure 28 back through optical probe 56 and sent back through optical fiber 54S and recollimated by fiber collimator 52 to form the reflected light portion of sample arm collimated beam 18S. As in low-coherence interferometer 110, the reflected light portions of the reference and sample arm collimated beams 18R and 18S of low-coherence interferometer 110A are recombined at the 50/50 beam splitter 24 to form a collimated low-coherence interference beam. The rest of the interferometer apparatus 100 and 100A are the same with identical functions. As with the input optical fiber 14, optical fiber 54S is preferably a single mode photonic crystal fiber (PCF) since it will function properly over the entire wavelength range of the tunable filter 12. The optical probe 56 can be readily configured to be portable or hand-held and readily aligned so that it is normal to the top surface of the multilayer structure 28. Hand-held probes are usually designed with a standoff distance that matches the focal length of the probe, so that when in contact with the top surface of the multilayer structure 28 the structure is automatically placed in the measurement region of the interferometer apparatus. Using an optical probe in the sample arm of the interferometer enables the interferometer apparatus to be portable so that it can be used to measure multilayer structures in their native environments such as building windows, automotive windows and aerospace windows. The optical probe can also be mounted to translation stages so that it can be moved over the surface of the multilayer structure 28.

Figure 1B:
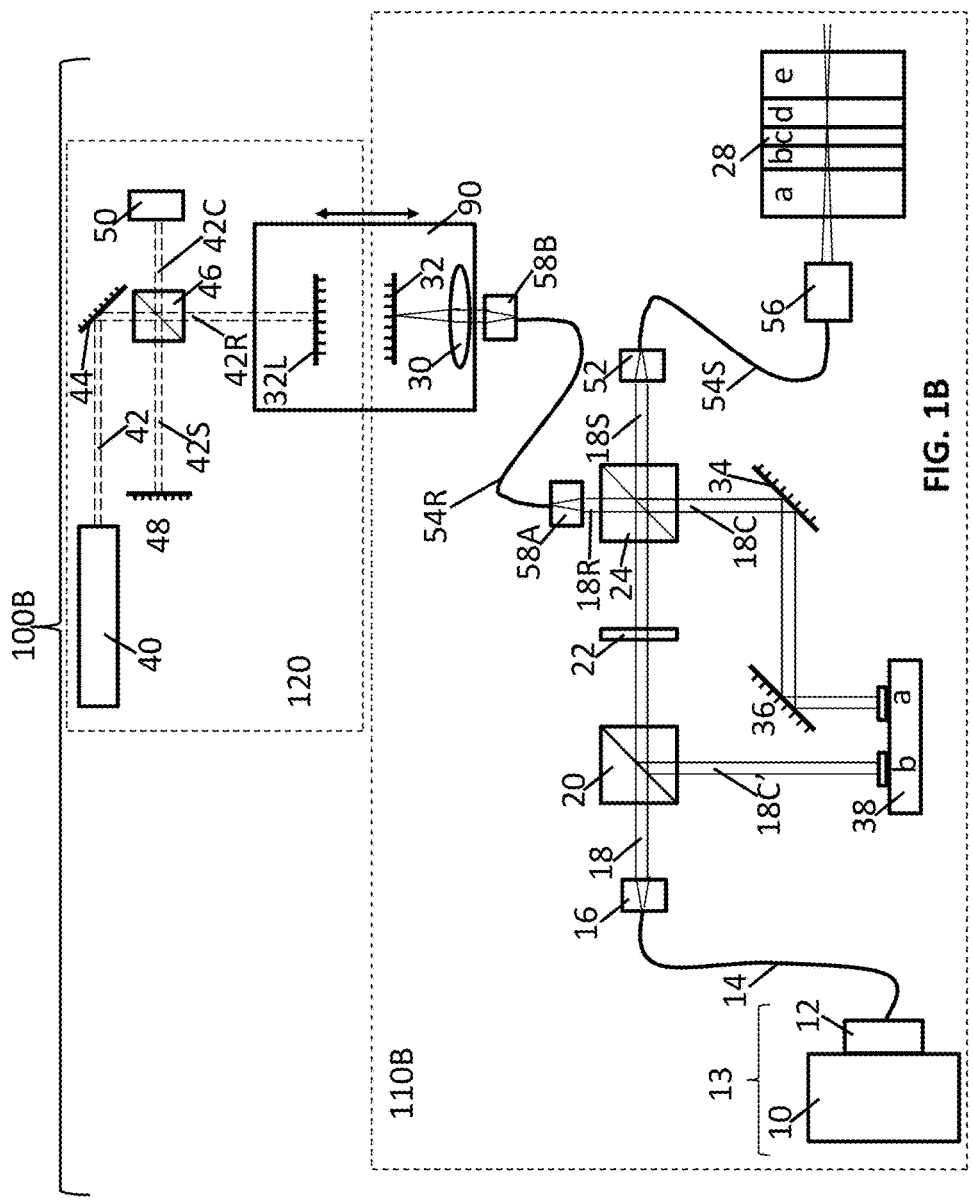
FIG. 1B shows a schematic of a third embodiment of an interferometer apparatus used to measure the optical thickness of each of the layers in a multilayer structure as a function of wavelength.

FIG. 1B shows a third embodiment of a dual interferometer apparatus 100B used to measure the optical thickness of each of the layers in a multilayer structure 28 as a function of wavelength. Most of the components of dual interferometer apparatus 100A and 100B are the same, and all components of the laser interferometer 120 are the same in both embodiments. The only differences in the components between low-coherence interferometer 110A and low-coherence interferometer 110B occur in the reference arm of the low-coherence interferometer 110B. Instead of the incident light portion of reference arm collimated beam 18R being directly incident on the reference arm lens 30 as shown in FIG. 1 and FIG. 1A, the incident light portion of reference arm collimated beam 18R shown in FIG. 1B part of the collimated beam 18R region is coupled into a fiber collimator 58A and transmitted through optical fiber 54R and coupled into a second fiber collimator 58B before being incident on reference arm lens 30 which then focuses the incident reference arm light onto reference mirror 32. Most of the light that is focused on reference mirror 32 passes back through reference arm lens 30, back through fiber collimator 58B, and transmitted back through optical fiber 54R and is recollimated by fiber collimator 58A to form the reflected light portion of reference arm collimated beam 18R. As in low-coherence interferometer 110, the reflected light portions of the reference and sample arm collimated beams 18R and 18S of low-coherence interferometer 110A are recombined at the 50/50 beam splitter 24 to form a collimated low-coherence interference beam. The rest of the dual interferometer apparatus 100A and 100B are the same with identical functions. As with the sample arm optical fiber 54S, optical fiber 54R is preferably a single mode photonic crystal fiber (PCF) since it will function properly over the entire wavelength range of the tunable filter 12. The dual interferometer configuration shown in FIG. 1B is preferred when the multilayer structure 28 needs to be tested remotely from the rest of the dual interferometer apparatus 100B. It is usual practice to match the optical path lengths of the sample and reference arm optical fibers 54S and 54R to minimize dispersion effects in the low coherence interferometer.

The laser interferometer 120 is shown at the upper portion of FIG. 1, FIG. 1A and FIG. 1B. A collimated light beam 42 is emitted from a laser 40, preferable a 632 nm HeNe laser. The collimated light beam 42 is incident on a 45° mounted mirror 44 and is incident on a beamsplitter 46, preferably a 50/50 beamsplitter cube. The beam splitter 46 splits the collimated laser beam 42 into sample and reference collimated laser beams 42S and 42R that are incident on stationary mirror 48 and laser reference mirror 32L respectively. Collimated laser light reflecting back from the laser reference mirror 32L and the stationary mirror 48 are recombined at the beam splitter 46 and are incident on a detector 50. As described above, the laser reference mirror 32L is co-mounted with the reference arm lens 30 and reference mirror 32 of low-coherence interferometer 110 on the variable optical path delay element 90. This causes the low-coherence interferometer and the coherent light interferometer to be coupled so that the optical path difference between the two arms in each of the respective interferometers changes by the same amount as a function of travel of the variable optical path delay element 90. In a preferred embodiment, reference mirror 30 and laser reference mirror 32L are comprised of the front and back surfaces of a single optically flat dual sided mirror. The laser interferometer 120 acts as a reference interferometer which is used to accurately track the optical path difference between the two arms in the low-coherence interferometer 110.

Figure 2:
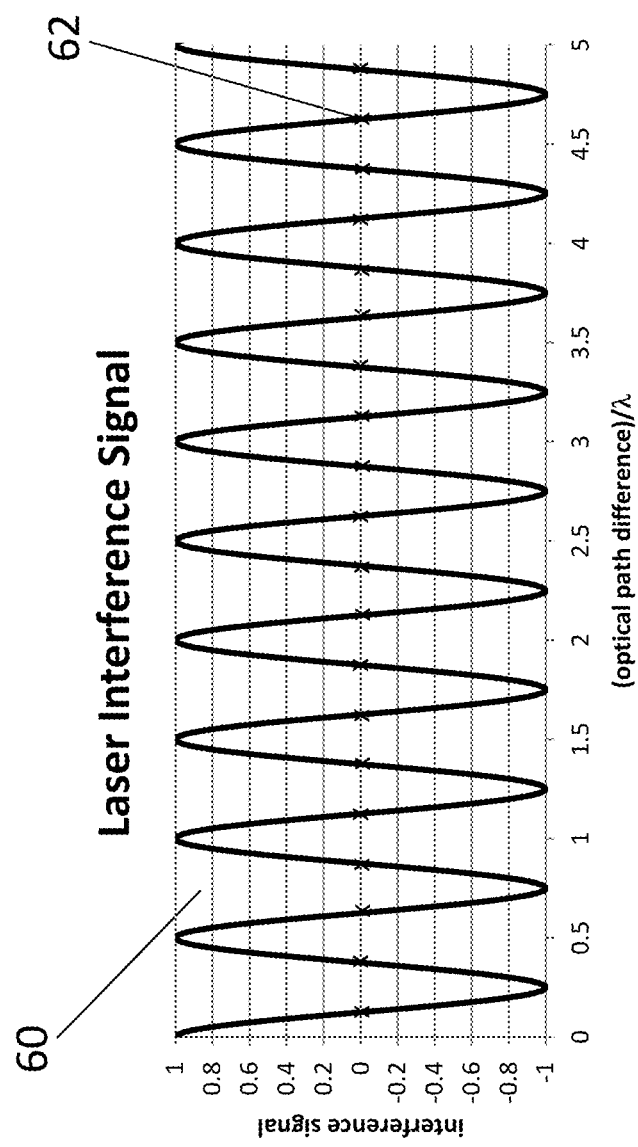
FIG. 2 shows a laser interferometer signal as a function of optical path length difference between the sample and reference arms in the interferometer.

During operation of the dual interferometer apparatus 100, 100A and 100B, the variable optical path delay element 90 is repetitively scanned at nearly constant velocity from a start position to an end position followed by scanning from the end position to the start position. The variable optical path delay element is typically actuated with a trapezoidal profile in which there is an acceleration phase, a constant velocity phase to within ±10% and a deceleration phase. Since the laser 40 has a very long coherence length, constructive interference occurs in the laser interferometer 120 whenever the difference in the path length between the stationary reference arm and the moving arm differ by $m\lambda/2$ where m is an integer and $\lambda$ is the wavelength of the laser light source, as shown in FIG. 2. FIG. 2 shows an example laser interferometer signal 60 as a function of optical path difference between the two arms of the interferometer normalized to the wavelength $\lambda$ of the laser. The optical path difference from the start of each scan and velocity of the laser and low coherence interferometers are the same at all times. Locations of the zero crossings 62 of the laser interferometer signal 60 measured with detector 50 as shown in FIG. 2 can be used as a distance scale to trigger data acquisition of the low coherence interferometer balanced detector (BD) signal at known distance intervals. Locations of the maxima and minima of the laser interference signal 60 can also be used as the distance scale. Thus, the reference interferometer is used to accurately track the location of the variable optical path delay element as it is repetitively scanned.

Figure 3:
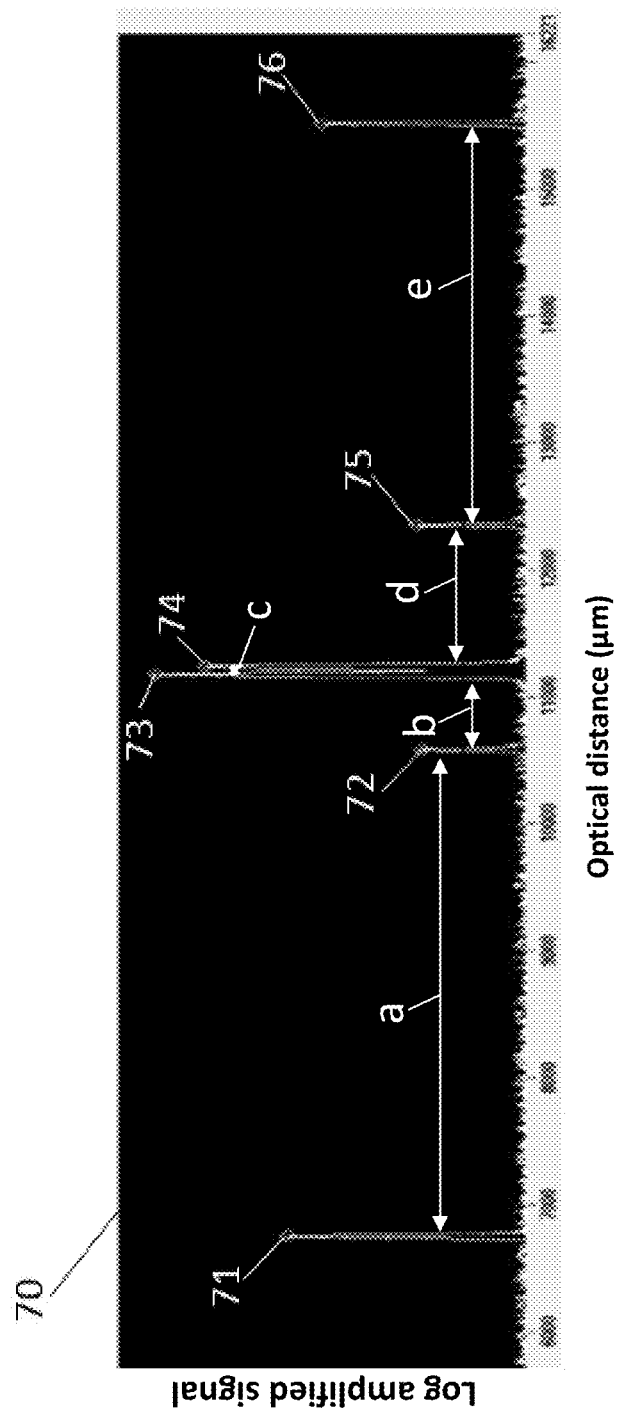
FIG. 3 shows an example low-coherence interferometer scan as a function of optical scan distance of the reference arm of the interferometer.

Constructive interference occurs in the low coherence interferometer 110 when the optical path length from the beam splitter 24 to the reference mirror 32 is equal in length to the optical path length from the beam splitter 24 to an optical interface of the multilayer structure 28 within a few coherence lengths of the low coherence light source 10, which is typically on the order of 5-25 μm. In order to be able to observe all of the optical interfaces in the multilayer structure 28, the variable optical path delay element 90 must travel a distance greater than the total optical path in the multilayer structure 28. Also, the optical path length from the beam splitter 24 to the reference mirror 32 at the start position of the reference mirror 32 is required to be less than the optical path length from the beam splitter 24 to the first optical interface (air/28a) in the multilayer structure 28 and the optical path length from the beam splitter 24 to the reference mirror 32 at the end position of the reference mirror 32 is required to be greater than the optical path length from the beam splitter 24 to the last optical interface (28e/air) in the multilayer structure 28. As the variable optical path delay element 90 is moved from its start position to its end position all of the optical interfaces in the multilayer structure will be observed, an example of which is shown in FIG. 3. In addition, when the variable optical path delay element 90 is scanned from its end position to its start position all of the optical interfaces in the sample will be observed in reverse order. The distance between the start position and the end position is larger than the total optical thickness of the m layer multilayer structure.

Data from the balanced detector 38 is filtered, log amplified and the envelope of the log amplified low coherence interferometer signal is digitized as a function of distance using a high-speed data acquisition card and is displayed and recorded. FIG. 3 shows an example low coherence interferometer scan 70 (also called an interferogram) as a function of optical scan distance of the variable optical path delay element 90 showing the locations of all of the optical interfaces in an exemplary 5-layer multilayer structure 28 using the filtered low-coherence light source centered at 650 nm. The log amplified signal coming from the balanced detector 38 is shown as a function of optical distance referenced from the location of the start of the scan. The optical scan distance is calculated from the measured laser interferometer signal. Peaks 71, 72, 73, 74, 75 and 76 are observed at the locations of each optical interface in the multilayer structure 28 and correspond to the air/28a, 28a/28b, 28b/28c, 28c/28d, 28d/28e and 28e/air interfaces respectively. In the 5-layer structure, there are 6 optical interfaces and in general for a m layer multilayer structure there are m+1 optical interfaces including the top and bottom air interfaces of the multilayer structure. The distances between successive optical interfaces shown by letters a, b, c, d and e correspond to the optical thickness of each of the layers 28a, 28b, 28c, 28d and 28e respectively. Since the low coherence interferometer data is sampled at known distance intervals, peak location algorithms can be applied to find the true locations of all of the peaks in the low-coherence interferometer data. For example, when using a low coherence source that has a Gaussian wavelength profile, the amplified signal also has a Gaussian envelope and with log amplification the signal at each peak looks like a quadratic function. Multiple measured points around the peak could then be fit to a quadratic function to find the true location of the peak. Multiple scans are averaged and statistics for measurement reproducibility are obtained. Table 1 shows the measured optical thickness for each of the 5 layers of the multilayer structure measured in FIG. 3 along with its standard deviation for 100 repeat measurements.

TABLE 1

650 nm optical thickness and standard deviation for a 5-layer structure.

| Layer # | Optical Thickness (μm) | Standard Deviation (μm) |
|---|---|---|
| 1 | 3857.52 | 0.16 |
| 2 | 500.94 | 0.17 |
| 3 | 62.60 | 0.06 |
| 4 | 1112.14 | 0.20 |
| 5 | 3162.65 | 0.19 |

When measuring a multilayer structure, the multilayer structure 28 is mounted in front of and normal to the lens 26 shown in FIG. 1 or optical probe 56 shown in FIG. 1A and FIG. 1B. This allows the low-coherence incident light to be focused inside the multilayer structure and to maximize the magnitude of the light reflected back from each optical interface of the multilayer structure 28. A sequence of measurements is performed at the same location in the multilayer structure 28 having m layers to measure the optical thickness of each of the m layers in the multilayer structure as a function of wavelength. Multiple scans are measured at each wavelength and averaged. The sequence of measurements is made by setting the tunable filter 12 to transmit light of a first center wavelength $\lambda_1$ followed by changing the center wavelength range of the tunable filter 12 by known increments, preferably in the range of 5-10 nm wavelength intervals over the entire wavelength range of the measurements which is preferably over the range of 400-840 nm for many materials. As an example, if we select 5 nm wavelength intervals throughout the wavelength range of 400-840 nm there will be 89 distinct wavelengths chosen for measurement. We use the convention that the shortest center wavelength for the filtered light source is $\lambda_1$ and the longest wavelength used for the filtered light source is $\lambda_k$ where k is the number of different wavelengths used to measure the optical thicknesses of each of the layers in the multilayer structure. For each center wavelength of the tunable filter 12 $\lambda_j$ where j=1 to k, the resultant measured optical thicknesses are $[n_{g1}(\lambda_j)t_1], [n_{g2}(\lambda_j)t_2], \ldots [n_{gm}(\lambda_j)t_m]$ for each of the m layers in the multilayer structure 28. The center wavelength for each successive $\lambda_j$ is longer than $\lambda_{j-1}$.

The measured optical thicknesses of each layer include the physical thicknesses $t_1, t_2 \ldots t_m$ of each of the m layers in the multilayer structure 28 which are independent of each other and the measurements at each measurement wavelength $\lambda_j$ are performed without moving the sample the physical thicknesses $t_1, t_2 \ldots t_m$ do not change with the measurement center wavelength of the light source $\lambda_j$. This allows us to select one center measurement wavelength as a reference wavelength which we call $\lambda_o$, and we can calculate the ratio of measured optical thickness at each measurement wavelength to that measured at the selected reference wavelength $\lambda_o$. Since the same layer physical thickness appears in the numerator and the denominator, the ratio of optical thickness ratio at wavelength $\lambda_j$ for the ith layer is equal to the normalized group index of refraction $\overline{n_{gi}}(\lambda_j)$ of the ith layer where i=1 to m is given by the relationship $$\overline{n_{gi}}(\lambda_j) = \frac{[n_{gi}(\lambda_j)t_i]}{[n_{gi}(\lambda_o)t_i]} = \frac{[n_{gi}(\lambda_j)]}{[n_{gi}(\lambda_o)]}. \tag{1}$$

The wavelength dependence of the normalized group index of refraction $\overline{n_{gi}}(\lambda_j)$ for each of the m layers of the multilayer structure as a function of wavelength $\lambda_j$ where j=1 to k defines the normalized group index of refraction dispersion curve of the material in the ith layer over the wavelength range of the measurement.

We have found that the normalized group index of refraction dispersion curve is unique for most materials as described in detail below. Thus, the shape of the measured normalized group index of refraction dispersion curves for each of the m layers can be used to identify the material composition of each of layer. Material identification can be done by comparing the measured normalized group index of refraction dispersion curves at the measured center wavelengths $\lambda_j$ where j=1 to k to those found in a material database of reference materials with known normalized group index of refraction dispersion curves with data points at the same set of center wavelengths and performing a statistical best fit analysis. The reference data base of known materials must include the group index of refraction dispersion curve data since the normalized group index of refraction dispersion curve is derived from it as shown in Equation 1.

The reference data base of known materials is required to include the group index of refraction dispersion curves for all materials in the data base to enable determination of physical thickness from measured optical thickness measurements. Once the material is identified from its known normalized group index of refraction dispersion curve we can then look up its group index of refraction dispersion curve at each of the measured center wavelengths $\lambda_j$ and calculate the layer physical thickness by dividing the measured optical thickness data by the group index of refraction for the material at each measured wavelength $\lambda_j$.

There are two methods of getting data from different materials into a normalized group index of refraction database using a reference wavelength $\lambda_o$. The first method uses published data bases of phase refractive index data versus wavelength and then calculates the group index of refraction and normalized group index of refraction dispersion curves from the published data and equations. The second method uses a group index of refraction cell attached to the measurement apparatus used in the practice of this invention, an embodiment of which is shown in FIGS. 7A and 7B. These two methods are described below.

Figure 4:
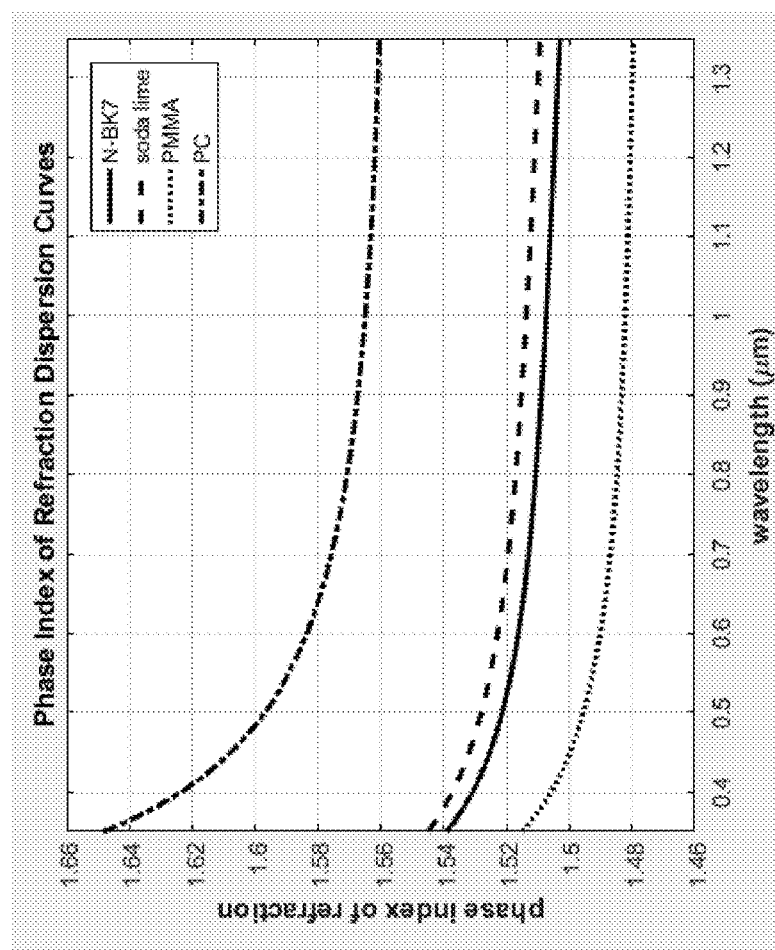
FIG. 4 shows phase index of refraction dispersion curves for some different materials.

The phase index of refraction is related to the property of optical dispersion. The phase index of refraction dispersion curve has been found to be unique for most optical materials. Instruments for measuring the wavelength dependence of the phase index of refraction which is called a dispersion curve include spectral ellipsometers, spectral goniometers and refractometers. A published data base of the phase index of refraction dispersion curves for various materials can be found at M. N. Polyanskiy, "Refractive Index Database", https://refractiveindex.info (subsequently herein "Polyanskiy"). Optical dispersion in optical materials is the phenomenon in which the phase velocity $v_p(\lambda)$ of a wave depends on the wavelength of light $\lambda$ traveling through the optical material. The phase index of refraction $n_p(\lambda)$ of a material is defined as $$n_p(\lambda) = \frac{c}{v_p(\lambda)} \quad (2)$$

where c is the speed of light in vacuum and $v_p(\lambda)$ is the phase velocity. A plot of index of refraction as a function of wavelength is called a dispersion curve. FIG. 4 shows example phase index of refraction versus wavelength data for some example materials including soda lime glass, Schott N-BK7 borosilicate glass, poly(methyl methacrylate) PMMA and polycarbonate (PC) based on the Sellmeier equation from Polyanskiy for each of these materials.

Figure 5:
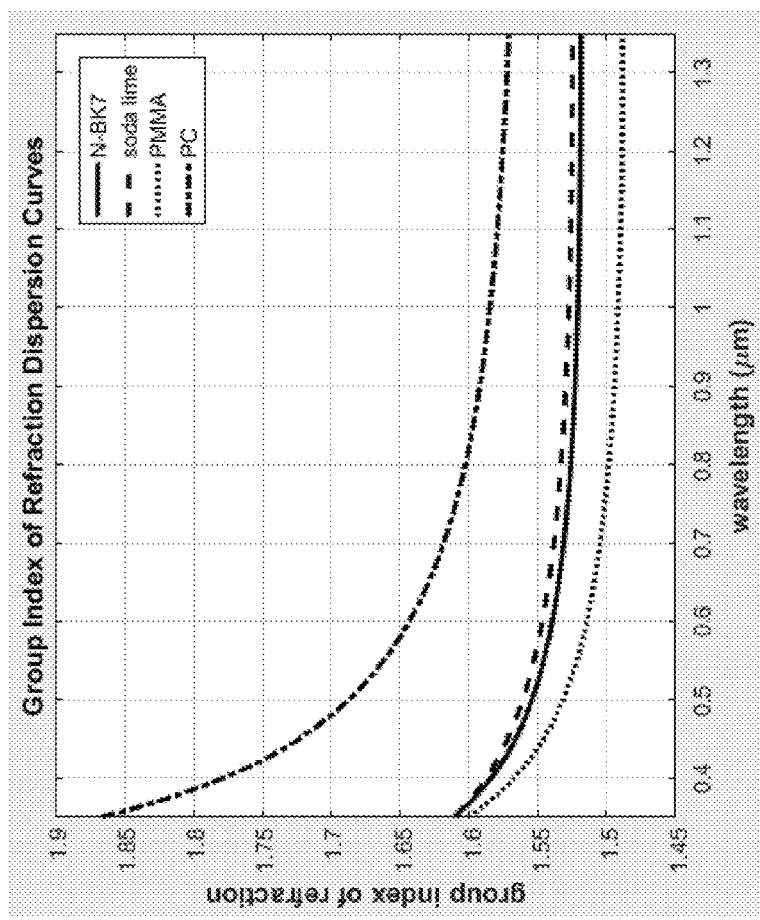
FIG. 5 shows group index of refraction dispersion curves for some different materials.
Figures 6A, 6B:
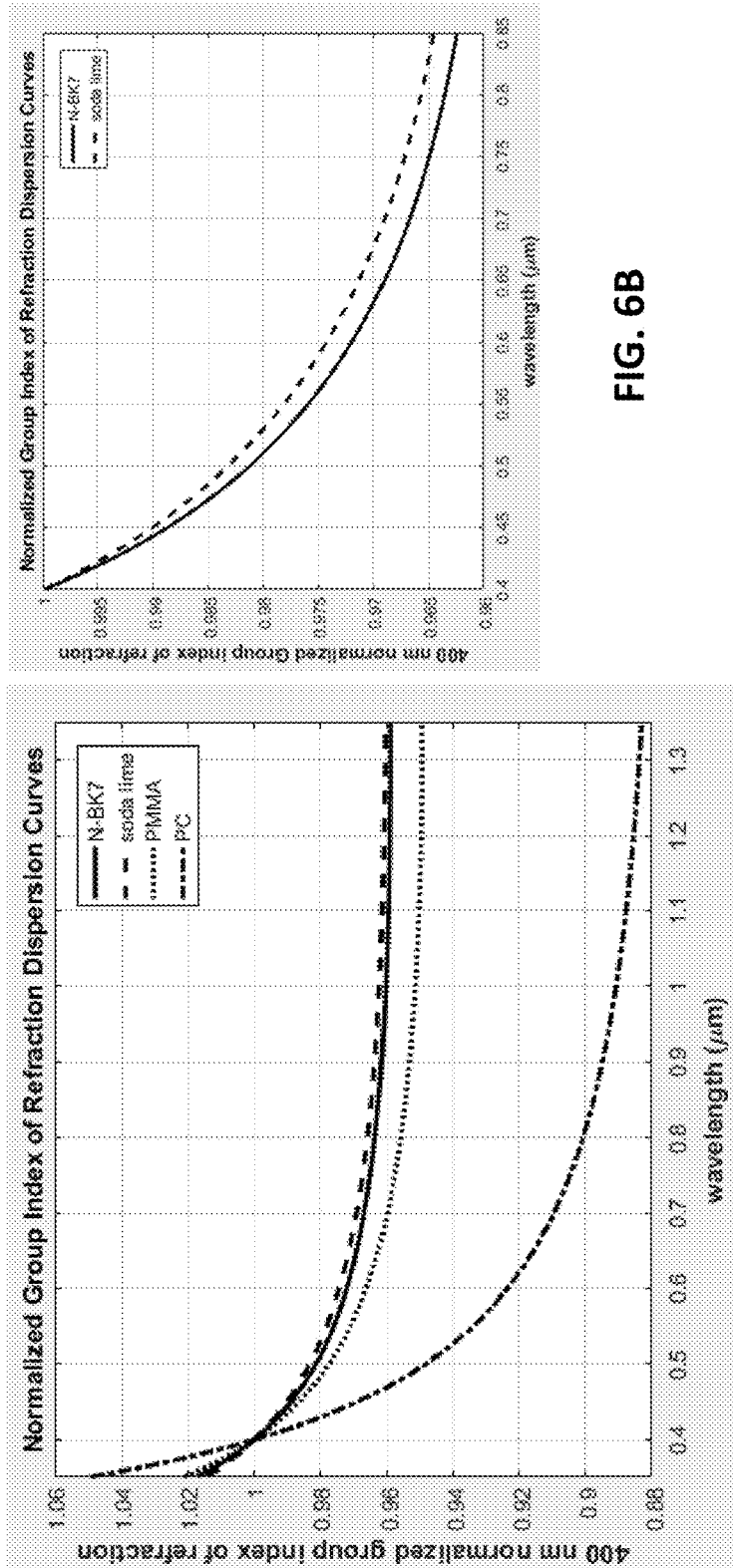
FIG. 6A shows normalized group index of refraction dispersion curves for some materials.
FIG. 6B shows an expanded region of the normalized group index of refraction dispersion curves for two of the materials shown in FIG. 6A.

The group index of refraction of a material is related to the phase index of refraction by the relationship $$n_g(\lambda) = n_p(\lambda) - \lambda \frac{dn_p(\lambda)}{d\lambda} \quad (3)$$

where $n_g(\lambda)$ is the group index of refraction and $dn_p(\lambda)/d\lambda$ is the derivative of the phase index of refraction as a function of wavelength $\lambda$. FIG. 5 shows the calculated group index of refraction dispersion curve for the same set of materials shown in FIG. 4. FIG. 6A shows the normalized group index of refraction dispersion curve $\overline{n}_g(\lambda)$ calculated from the relationship $$\overline{n}_g(\lambda) = \frac{n_g(\lambda)}{n_g(\lambda_o)} \quad (4)$$

using 400 nm as the reference wavelength $\lambda_o$ for the same set of materials shown in FIG. 4 and FIG. 5. FIG. 6B shows an expanded view of the normalized group index of refraction dispersion curves for N-BK7 and soda lime glass over the range of 400 nm to 850 nm.

We can add a known material to the group index of refraction reference data base of known materials by first calculating the group index of refraction as a function of wavelength from the phase index of refraction data using Equation 3 and then extracting the calculated values of group index of refraction at the same set of k distinct center wavelengths of the tunable light source defined as $\lambda_j$ where j is an integer and j=1 to k inclusively with $\lambda_1$ being the shortest center wavelength of the tunable light source and $\lambda_k$ being the longest wavelength of the tunable light source that are used in all measurements.

The second method of getting data from different materials into a normalized group index of refraction database using a reference wavelength $\lambda_o$ uses a group index of refraction measurement cell attached to the measurement apparatus an embodiment of which is shown in FIGS. 7A and 7B. A single layer of the known material sample must be first obtained with approximately parallel (within ±3°) top and bottom surfaces. FIG. 7A shows the group index of refraction cell with the known material sample 82 present and FIG. 7B shows the group index of refraction cell without the known material sample 82 being present. The optical probe 56 shown in FIG. 7A and FIG. 7B is the same optical probe 56 that is attached to the sample arm optical fiber 54S of the dual interferometer embodiments shown in FIG. 1A and FIG. 1B. The optical probe 56 is mounted at a fixed distance above a measurement cell 80 which is used to determine group index of refraction dispersion curves and normalized group index of refraction dispersion curves of single layers of different materials. Two sets of measurements are required, a first set with a single layer known material sample 82 present in the measurement cell 80 and a second set of measurements without the known material sample 82 being present as described below.

The group index of refraction measurement cell 80 is comprised of a top flat 84 having a bottom optically flat surface $F_1$ and a bottom optical flat 86 having a top optically flat surface $F_2$ separated by a spacer 88 containing a cavity 78 between the bottom optically flat and the top optically flat surfaces $F_1$ and $F_2$. The spacer 88 causes the separation of surfaces $F_1$ and $F_2$ to be at a constant physical distance $d_o$ (also called the total gap) as shown in FIG. 7B. The spacer 88 also contains a receiving surface RS at a distance $d_2$ above the top optically flat surface $F_2$ of the bottom optical flat 86 for disposing the single layer known material sample 82 at a fixed position in cavity 78. The optically flat surfaces F1 and F2, the upper and lower surfaces of the spacer 88, and the receiving surface RS are constructed to be parallel to each other. The receiving surface RS divides the cavity into a larger diameter upper cavity between surfaces $F_1$ and RS and a smaller diameter lower cavity between surfaces RS and $F_2$. Typical dimensions for the diameters of the upper and lower parts of the cavity are 30-150 mm and 5-25 mm respectively. The known material sample 82 is required to be flat so that is has top and bottom surfaces which are nominally parallel to each other within a few degrees. The measurement cell 80 preferably includes a thermal control system (not shown) including a thermostat (not shown) to cause the measurement cell 80 to remain at a constant known temperature (±0.1° C.) throughout each set of measurements. Typical dimensions of the distance between surface $F_1$ and $F_2$ of cavity are 5-50 mm. The optical probe 56 is also normally aligned with respect to the optically flat surfaces of the measurement cell 80. The known material sample should have a physical thickness of at least 10 μm and can be as thick as 40 mm or more and is preferably in the range of 0.1 to 10 mm in physical thickness.

The following measurement procedure is used to add a new material to the group index of refraction dispersion curve and normalized group index of refraction dispersion curves of a new material to the reference data base of known materials. A single layer known material sample 82 of a material to be added to the database is first disposed into the measurement cell 80 at the receiving surface RS. The sample must be large enough so that it does not fall into the lower part of the cavity between the receiving surface RS and the top surface $F_2$ of the bottom optical flat 86. During the first part of the measurement shown in FIG. 7A the known material sample 82 is mounted onto the receiving surface RS of the measurement cell 80 with the dual interferometer measuring at the same set of k distinct center wavelengths of the tunable light source $\lambda_j$ where j is an integer and j=1 to k inclusively with $\lambda_1$ being the shortest center wavelength of the tunable light source and $\lambda_k$ being the longest wavelength of the tunable light source as used when measuring unknown multilayer structures 28.

From the geometry in FIG. 7A, the optical interfaces that are observed in sequence during a low-coherence interferometer scan are the bottom surface $F_1$ of the top optical flat 80, the top surface of known material sample 82, the bottom surface of known material sample 82 and the top surface $F_2$ of bottom optical flat 86. The physical distance between the bottom surface $F_1$ of the top optical flat 80 and the top surface of known material sample 82 is defined as $d_1$ (the top gap), the physical distance between the top surface of known material sample 82 and the bottom surface of known material sample 82 is $t_m$, and the physical distance between the bottom surface of known material sample 82 and the top surface $F_2$ of bottom optical flat 86 is $d_2$ (the bottom gap). The known material sample 82 has a group index of refraction $n_{gm}(\lambda_j)$ at each measured wavelength of the tunable source where j=1 to k and the air inside the cavity air has an index of refraction $n_a(\lambda_j)$. For each measured wavelength $\lambda_j$, the measured optical thicknesses $T_1$, $T_2$ and $T_3$ are $$T_1(\lambda_j)=[n_a(\lambda_j)d_1(\lambda_j)], \; T_2(\lambda_j)=[n_{gm}(\lambda_j)t_m(\lambda_j)], \; T_3(\lambda_j)=[n_a(\lambda_j)d_2(\lambda_j)] \quad (5)$$

where $d_1$ and $d_2$ are the top and bottom physical air gap thicknesses, respectively, in the measurement fixture above and below the sample, and $n_a(\lambda_j)$ is the group index of refraction of air at the measurement wavelength. After these three parameters are measured as a function of wavelength over the range of 400 nm-840 nm, the sample is removed from the cell as shown in FIG. 7B and the optical distance $[n_a(\lambda)d_o]$ is measured as a function of wavelength $\lambda$. The cavity 78 gap physical distance $d_0$ (gap) is then calculated at all of the measured wavelengths $\lambda_j$ by the relationship $$d_o(\lambda_j) = \frac{[n_a(\lambda_j)d_o]}{n_a(\lambda_j)} \quad (6)$$

where $d_o(\lambda_j)$ is the measured value of physical distance $d_o$ using center wavelength $\lambda_j$.

Figure 8:
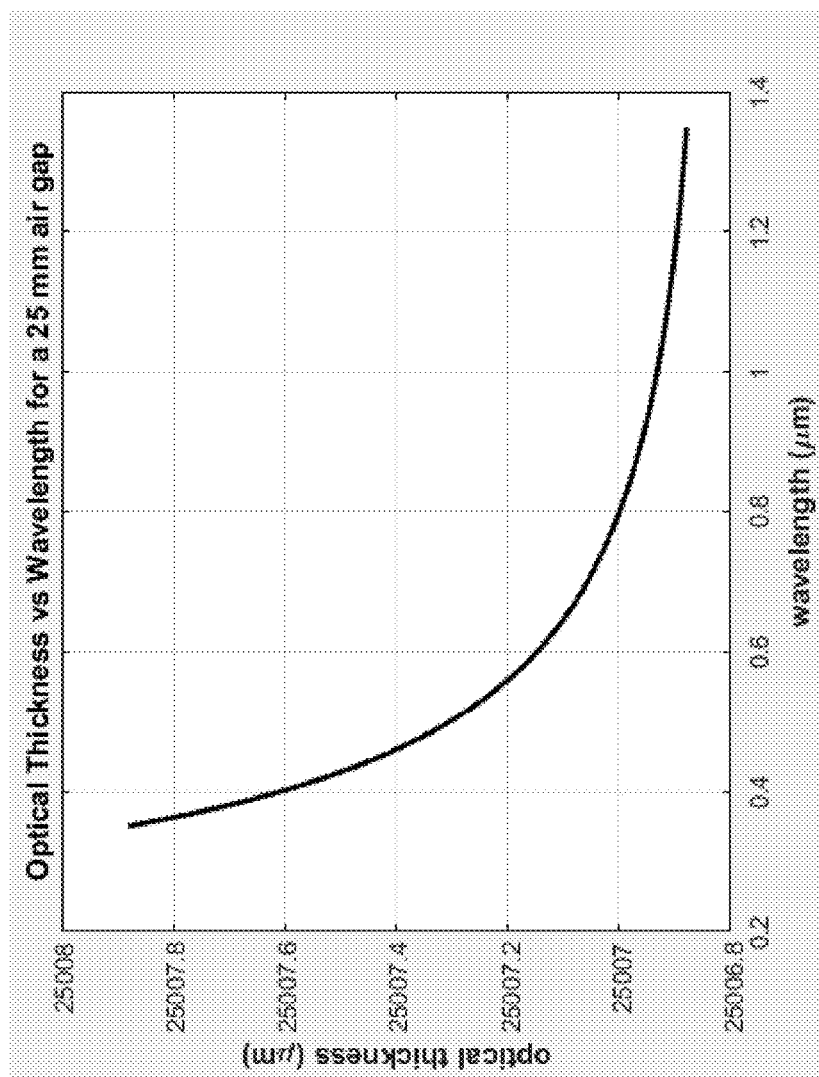
FIG. 8 shows a plot of the expected optical thickness of a 25 mm air gap as a function of wavelength.

Similarly the top and bottom air gap distances $d_1$ and $d_2$ shown in FIG. 7A can be found from the relationships $$d_1(\lambda_j) = \frac{[n_a(\lambda_j)d_1]}{n_a(\lambda_j)}; \text{ and } d_2(\lambda_j) = \frac{[n_a(\lambda_j)d_2]}{n_a(\lambda_j)} \quad (7)$$

where $d_1(\lambda_j)$ and $d_2(\lambda_j)$ are the measured values of physical distances $d_1$ and $d_2$ using center wavelength $\lambda_j$. The phase and group index of refraction of air have been well characterized as a function of wavelength and temperature as described by Jack A. Stone and Jay H. Zimmerman, in the NIST, Engineering Metrology Toolbox, "Index of refraction of air" which can be found at http://emtoolbox.nist.gov/Wavelength/Documentation.asp. FIG. 8 shows a plot of the expected optical thickness for a 25 mm physical air gap distance $d_o$ as a function of wavelength at 20° C.

Temperature control of the measurement cell 80 is important for accurate measurements. The group and phase index of refraction of most materials are slightly temperature dependent. The refractive index of air is 1.0002684 at 20° C. and 1.0002637 at 25° C., and the change with temperature is $-9.43 \times 10^{-7}$/° C. at 20° C. and $-9.22 \times 10^{-7}$/° C. at 25° C. For the 25 mm physical path length cuvette measured in air, a 1° C. temperature change will result in a 23.6 nm error in the calculation of the physical path length $d_o$ of the cavity 78 in the measurement cell 80 when measured at 20° C., and a 23.1 nm error when measured at 25° C. Most other optical materials including glasses and plastics have larger changes in refractive index with temperature than air. As examples the change in refractive index with temperature near room temperature for acrylic materials is approximately $-8.5 \times 10^{-5}$/° C. and for N-BK7 glass refraction, the value is $1.6 \times 10^{-5}$/° C.

From the measured parameters $d_o$, $d_1$ and $d_2$, we can then calculate the physical thickness $t_m$ of the known material sample 82 from the relationship $$t_m(\lambda_j)=d_o(\lambda_1)-d_1(\lambda_j)-d_2(\lambda_j). \quad (8)$$

The physical distances $d_o$, $d_1$ and $d_2$ are independent of wavelength, and the statistical variation in the measured values as a function of wavelength is an indication of the instrument's measurement repeatability. The physical thickness of the material $t_m$ is also independent of wavelength. Once the physical thickness $t_m$ of the known material sample 82 is known, we can then calculate the group index of refraction at each of the measured wavelengths $\lambda_j$ of the known material sample 82 as a function of wavelength from the relationship $$n_{gm}(\lambda_j) = \frac{[n_{gm}(\lambda_j)t_m(\lambda_j)]}{t_m(\lambda_j)}. \quad (9)$$

Once we know the group index of refraction of the known material sample 82 as a function of wavelength, we can then add its group index of refraction dispersion curve to the known material database. The normalized group index of refraction dispersion curve is then also calculated using the standard reference wavelength $\lambda_o$. The measured group index of refraction as a function of wavelength for the measured material is first added to the reference material database of known material group index of refraction dispersion curves. The normalized group index of refraction dispersion curve for this material is now calculated by dividing the group index of refraction dispersion curve by the reference wavelength $\lambda_o$ as described above using Equation 4.

The reference data base of known materials also includes the derived group index of refraction Sellmeier equation for each of the known and measured materials which is given by the relationship $$n_g^2(\lambda) - 1 = \sum_i^m \frac{B_i \lambda^2}{\lambda^2 - C_i} \qquad (10)$$

where i and m are integers and i varies from 1 to m and $B_i$ and $C_i$ are constants. For most optical glasses, three sets of coefficients are used (m=3) and for many plastics only one set of coefficients is needed (m=1). The group index of refraction of known material samples 82 measured as a function of wavelength are converted to the Sellmeier form of Equation 10 by calculating the best fit coefficients $B_i$ and $C_i$ to the measured data.

The measurement cell 80 shown in FIG. 7A and FIG. 7B can also be used to measure the total physical thickness of a multilayer structure 28. The optical thickness of the total gap in the cell $d_o$ is first measured without the multilayer structure being present. Then the multilayer structure is placed in the measurement cell in the same location of the known material sample 82 and the optical thicknesses of the top air gap $d_1$ and the bottom air gap $d_2$ are measured as before and applying Equation 8 to get the total physical thickness. The total physical thickness measurement can become important to distinguish between two materials which have very close normalized group index of refraction profiles since they will generally have different group index of refraction values. Comparing the total physical thickness of the multilayer structure measured in the measurement cell with that obtained by identifying the best fit materials for each layer of the multilayer structure from their calculated normalized group index of refraction dispersion curves to a reference data base of known materials group index of refraction dispersion curves can also be used as a confirmation for the materials identification.

The measurement cell for measuring the total physical thickness of the multilayer structure 28 or a single layer known material sample 82 for adding a new material to the data base of known materials group index of refraction dispersion curves (both referred to as a test object) can also have a different structure to that shown in FIG. 7A and FIG. 7B. When the test object is installed in a suitable measurement cell, the measurement cell must have a top optically flat surface located above the top surface of the test object to form an upper airgap and a bottom optically flat surface located below the bottom surface of the test object to form a lower airgap. The requirements are that the two optically flat surfaces are parallel to each other and remain a fixed distance apart. The multilayer structure 28 is mounted between the top and bottom optically flat surfaces so that its outer surfaces at the location of measurement are nearly parallel to the top and bottom optically flat surfaces of the measurement cell. During measurements using the interferometer apparatus, the optical thickness of the upper airgap and the lower air gap are also measured along with the optical thickness of each of the observed layers in the test object as a function of wavelength of the low-coherence tunable light source.

Figure 9:
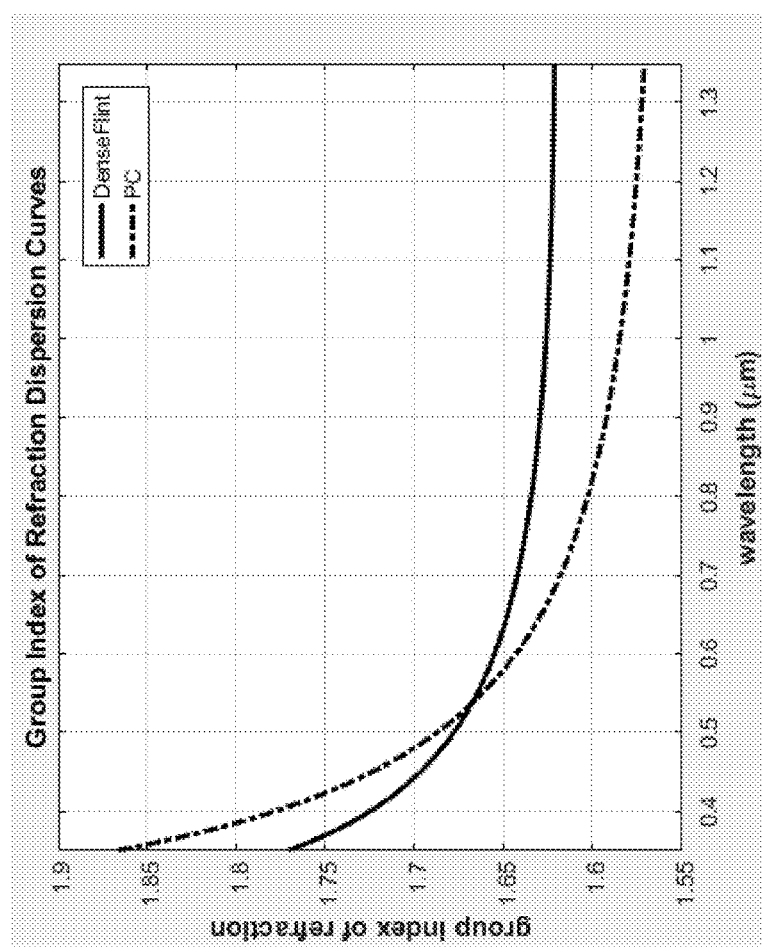
FIG. 9 shows group index of refraction dispersion curves for two materials that cross each other at 536.5 nm.

For an m layer sample the maximum number of observed optical interfaces will be m+1. Thus, the number of layers in the multilayer structure is equal to 1 less than the maximum number of optical interfaces measured in the sample as a function of incident wavelength $\lambda_j$ of the filtered low coherence light source 13. When measuring a multilayer optical structure having m layers there are usually m+1 optical interfaces observed in an interferometer distance scan. In some cases all of the optical interfaces in the multilayer structure may not be observed at all of the measured wavelengths $\lambda_j$. This occurs when the group index of refraction is the same or nearly the same for two adjacent layers in the multilayer structure 28. FIG. 9 shows an example of two group index of refraction dispersion curves for dense flint glass and for polycarbonate plastic in which the dispersion curves cross at a wavelength of 536.5 nm where both materials have a group index of refraction of 1.6682. For the dual low coherence interferometer apparatus 100, 100A, and 100B shown in FIG. 1, FIG. 1A, and FIG. 1B respectively, the individual optical interfaces for each layer will not be observable when the group index of refraction of two adjacent layers differ by less than about 0.001. For the example shown in FIG. 9, the instrument will not see the optical interface when for center wavelengths between 532.5-539.5 nm when dense flint glass is adjacent to polycarbonate plastic. When the ith and ith+1 layers of an m layer multilayer structure have the same group index of refraction to within 0.001 at a wavelength $\lambda_c$, no discernable optical interface will occur between the layers $i^{th}$ and the $i+1^{th}$ layers and the measured optical thickness of these layers will be $[n_{gi}(\lambda_c)t_i + n_{gi+1}(\lambda_c)t_{i+1}]$ and only m−1 layers will be observed in the measured interferogram similar to that shown in FIG. 3. The wavelength regions where less than the usual number of measured layers occur can be readily found in the analysis since there will be less than m+1 optical interfaces in the measured interferograms in these relatively narrow regions of the optical spectrum. It is also relatively easy to tell which optical interface is missing in the data by looking at its relative location in the interferogram scan. The optical thickness data for the two layers containing the missing optical interface can then be omitted from the normalized group index of refraction calculations described in Equation 1.

In order to determine how many layers are in the multilayer structure, we first determine the maximum number of optical interfaces observed in the interferometer scans as a function of center wavelength $\lambda_j$ of the filtered low coherence light source 13 as the center wavelength is varied from $\lambda_1$ to $\lambda_k$. Most of the scans at different center wavelengths will have the same number of optical interfaces observed in the multilayer structure which is equal to the maximum number of optical interfaces and equal to m+1 where m is the number of layers in the multilayer structure 28 being tested. In some multilayer structures one to a few wavelength regions will have fewer peaks. When this occurs, 1-3 adjacent center wavelengths could be missing an optical interface at regions when the group index of refraction of the adjacent layers cross each other as shown in the example of FIG. 9. The air-top layer interface and the bottom layer-air interface will always be observed since the index of refraction of all solid materials is always greater than one.

Figure 10:
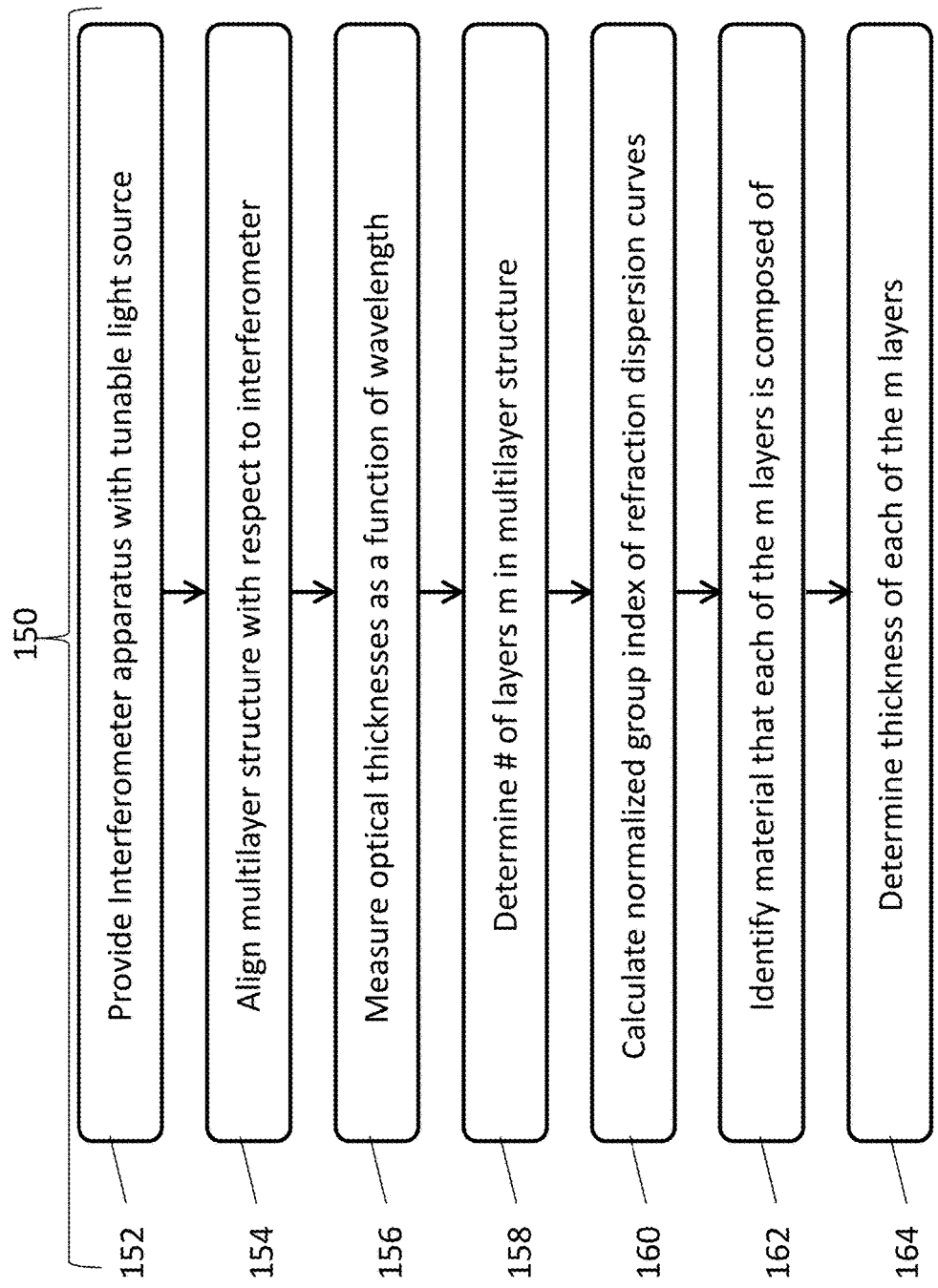
FIG. 10 shows a flow chart detailing the steps of the method used to identify the material composition of each layer in a multilayer structure and to determine each layer's physical thickness.

FIG. 10 is a flow chart 150 showing the steps performed in carrying out a method of identifying the material composition of each layer in a multilayer structure and to determine each layers physical thickness. The first Step 152 is to provide an interferometer apparatus with a tunable low-coherence light source. Suitable interferometer apparatuses 100, 100A and 100B have been described with reference to the descriptions of FIG. 1, FIG. 1A and FIG. 1B. Step 152 is followed by Step 154 in which the portion of the multilayer structure to be tested is aligned with respect to the interferometer apparatus. In some cases the multilayer structure will be set up in the measurement region of the instrument such as that shown in FIG. 1. In many cases the multilayer structure could be something mounted in its location of use such as a window in a vehicle, aircraft or a building and a portable interferometer apparatus having a portable optical probe is used to align the multilayer structure in situ. After the multilayer structure is mounted and aligned, Step 154 is followed by Step 156 in which the interferometer apparatus is used to measure the optical thickness of each of the observed layers in the multilayer structure as a function of center wavelength of the low-coherence tunable light source. A standard set of k center wavelengths $\lambda_j$ is selected where j=1 to $\lambda_1$ with being the shortest wavelength, $\lambda_k$ being the longest wavelength and each successive $\lambda_j$ is longer than $\lambda_{j-1}$. The locations of the peaks in interferometer scans obtained at each set of k wavelengths are determined and the scan distances between each successive optical interface define the optical thicknesses being measured. The total number of layers measured at each measurement wavelength $\lambda_j$ is noted in this Step. Step 156 is followed by Step 158 in which the number of layers m in the multilayer structure is determined. The number of layers m in the multilayer structure is set equal to the maximum number of layers observed in Step 156. Typically the number of observed layers m will be the same and equal to the maximum number of observed layers for all or almost all of the measured wavelengths $\lambda_j$ of the tunable low-coherence light source. Adjacent layers will not be observed at small wavelength ranges where their group index of refraction dispersion curves cross each other as discussed above during the discussion of FIG. 9. It is relatively easy to determine from the optical thickness data which layers are missing since the observed optical thickness will be the sum of the two adjacent layers optical thickness. Step 158 is followed by Step 160 in which the normalized group index of refraction dispersion curves are calculated for each of the m layers in the multilayer structure by selecting one center wavelength of the tunable light source as a reference wavelength and calculating the ratio of the measured optical thickness at each measurement wavelength to that measured at the selected reference wavelength for each of the m layers in the multilayer structure. Step 160 is followed by step 162 in which the material that each layer in the m layer multilayer structure is comprised of is identified by comparing its calculated normalized group index of refraction dispersion curve to a reference data base of known materials group index of refraction dispersion curves and finding the best fit material for each of the m layers in the multilayer structure. Step 162 is followed by Step 164 in which the physical thickness of each of the m layers of the multilayer structure is determined by dividing the measured optical thickness at each measured center wavelength of the tunable light source by the group index of refraction of the identified material at the respective measured center wavelength and calculating its average value for each of the m layers in the multilayer structure.

Figure 11:
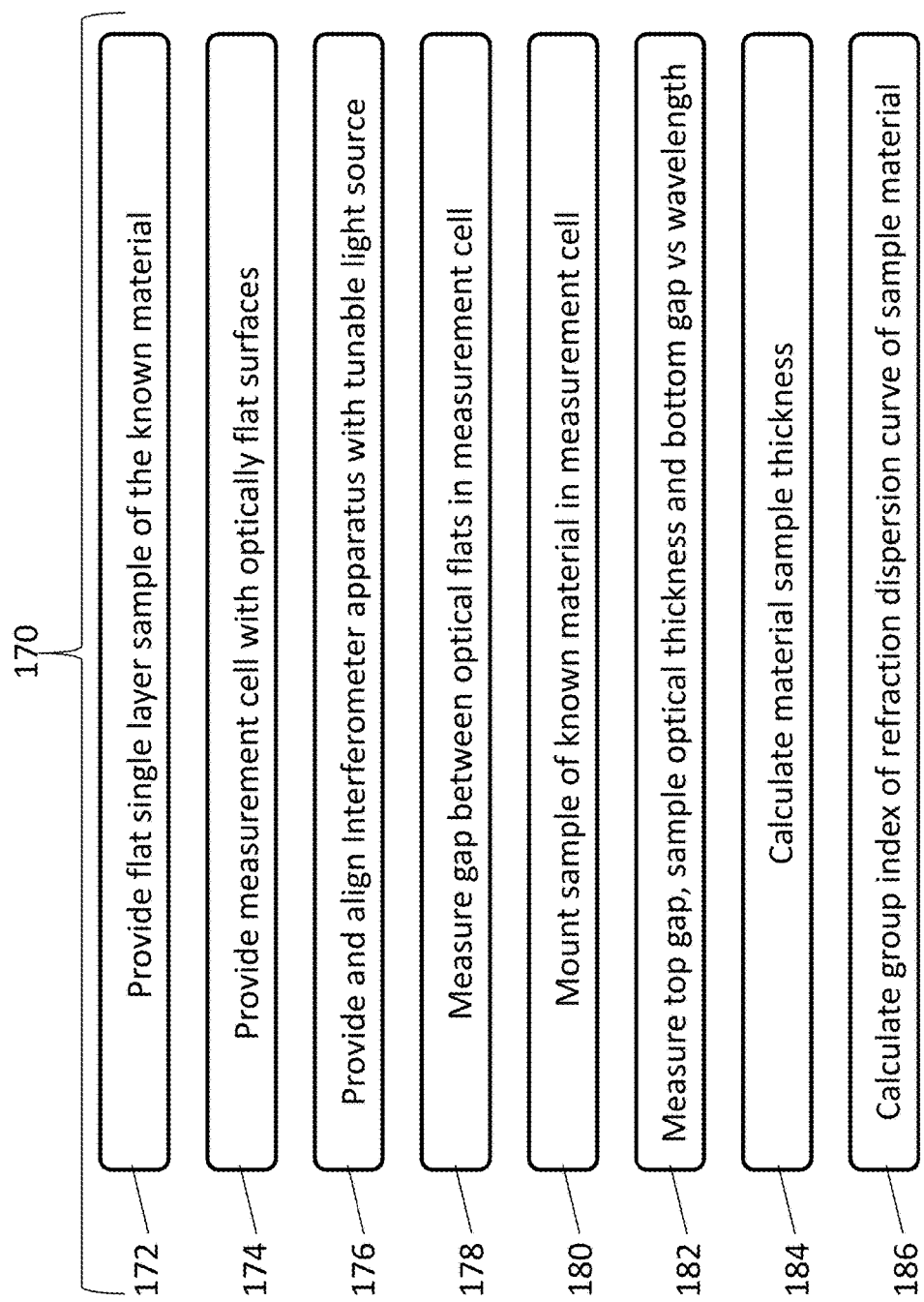
FIG. 11 shows a flow chart detailing the steps of the method to determine the group index of refraction dispersion curve for a known material.

FIG. 11 is a flow chart 170 showing the steps of a method to determine the group index of refraction dispersion curve for a known material. The first Step 172 is to provide a flat single layer sample of the known material. The flat single layer sample of the known material has the top flat surface separated from the bottom flat surface by the physical thickness of the known material. Step 172 is followed by Step 174 in which a measurement cell with optically flat surfaces is provided. The measurement cell will be comprised of a top flat having a bottom optically flat surface and a bottom optical flat having a top optically flat surface which are separated by a total gap larger than the physical thickness of the flat single layer sample, and the bottom and top optically flat surfaces are parallel to each other. Step 174 is followed by Step 176 in which an interferometer apparatus having a low-coherence tunable light source and an optical probe is provided and normally aligned to the optically flat surfaces of the measurement cell provided in Step 174. Step 176 is followed by Step 178 in which the gap between the bottom optically flat surface of the top flat and the top optically flat surface of the bottom flat of the measurement cell is determined. This measurement is performed by measuring the optical distance of the gap as a function of wavelength of the low-coherence tunable light source and dividing by the group index of refraction of air at each of the respective wavelengths and calculating the average value of the gap measured as a function of wavelength of the tunable light source. All Steps with measurements that are measured as a function of wavelength of the tunable light source are measured at the same set of k distinct center wavelengths of the tunable light source defined as $\lambda_j$ where j is an integer and j=1 to k inclusively with $\lambda_1$ being the shortest center wavelength of the tunable light source and $\lambda_k$ being the longest wavelength of the tunable light source. Each successive wavelength measured is at a longer wavelength than the previous one so that $\lambda_1 < \lambda_2 < \lambda_3 \ldots < \lambda_{k-1} < \lambda_k$. Step 178 is followed by Step 180 in which the sample flat single layer sample of the known material is mounted in the measurement cell in the gap between the bottom optically flat surface of the top flat and the top optically flat surface of the bottom flat. The flat single layer sample of known material is mounted so that it is parallel to the optically flat surfaces of the measurement cell. Step 180 is followed by Step 182 in which the interferometer apparatus is used to determine the top gap between the bottom optically flat surface of the top flat and the top surface of the known material sample, the optical thickness of the known material sample and the bottom gap between the bottom surface of the known material sample and the top optically flat surface of the bottom flat as a function of wavelength of the low-coherence tunable light source. The top gap and the bottom gap are determined by measuring the optical distance of the top and bottom gaps as a function of wavelength of the low-coherence tunable light source and dividing the top and bottom gap optical distances by the group index of refraction of air at each of the respective measured wavelengths and calculating the average values of the top and bottom gaps. Step 182 is followed by Step 184 in which the physical thickness of the flat single layer sample of the known material is determined. The physical thickness of the sample of known material is determined by subtracting the sum of the top gap and the bottom gap from the gap. Step 184 is followed by Step 186 in which the group index of refraction dispersion curve for the sample of known material is determined. This is done by dividing the optical thickness of the known material sample measured as a function of wavelength of the low-coherence tunable light source by the calculated physical thickness of the known material sample. The group index of refraction data measured as a function of wavelength for the new known material can then added to the database of known materials. The measured data as a function of wavelength for the new known material can also be put in the form of a Sellmeier equation by calculating the best fit Sellmeier coefficients $B_i$ and $C_i$ to the measured data.

Although the interferometer apparatus and examples have been described herein as including a dual interferometer in the standard Michelson configuration it is noted that other interferometer configurations can be utilized including Mach Zehnder configurations and autocorrelator mode configurations as described in Marcus '409. Also the reference interferometer can be replaced with a highly accurate optical encoder on the variable optical path delay element 90.

The invention has been described in detail with particular reference to certain example embodiments thereof, but it will be rather apparent to those skilled in the art that the foregoing detailed disclosure is intended to be presented by way of example only, and is not limiting. Various alterations, improvements, and modifications will occur to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims.

PARTS LIST

10 Broadband Low Coherence Light Source
12 Variable Wavelength Tunable Filter
13 Tunable Light Source
14 Optical Fiber
16 Fiber Collimator
18 Collimated Beam
18a Transmitted Low Coherence Interference Beam
18b Reflected Low Coherence Interference Beam
18f Focusing Low Coherence Beam
18r Reference Arm Collimated Beam
18s Sample Arm Collimated Beam
20 Polarizing Beam Splitter
22 Quarter Wave Plate
24 Beam Splitter
26 Sample Arm Lens
28 Multilayer Structure
28a First Layer
28b Second Layer
28c Third Layer
28d Fourth Layer
28e Fifth Layer
30 Reference Arm Lens
32 Reference Mirror
32l Laser Reference Mirror
34 Mirror
36 Mirror
38 Balanced Detector
38a First Detector
38b Second Detector
40 Laser
42 Collimated Laser Beam
42c Laser Interference Beam
42r Reference Arm Collimated Laser Beam
42s Sample Arm Collimated Laser Beam
44 Mirror
46 Beam Splitter
48 Mirror
50 Detector
52 Fiber Collimator
54s Sample Arm Optical Fiber
54r Reference Arm Optical Fiber
56 Optical Probe
58a Fiber Collimator
58b Fiber Collimator
60 Laser Interference Signal
62 Zero-Crossings
70 Low Coherence Interferometer Scan
71 First Optical Interface Location
72 Second Optical Interface Location
73 Third Optical Interface Location
74 Fourth Optical Interface Location
75 Fifth Optical Interface Location
76 Sixth Optical Interface Location
78 Cavity
80 Measurement Cell
82 Known Material Sample
84 Top Flat
86 Bottom Flat
88 Spacer
90 Variable Optical Path Delay Element
100 Interferometer Apparatus
100a Interferometer Apparatus
100b Interferometer Apparatus
110 Low-Coherence Interferometer
110a Low-Coherence Interferometer
110b Low-Coherence Interferometer
120 Laser Interferometer
150 Flow Chart
152 Step
154 Step
156 Step
158 Step
160 Step
162 Step
164 Step
170 Flow Chart
172 Step
174 Step
176 Step
178 Step
180 Step
182 Step
184 Step
186 Step

We claim:

1. A method of identifying the material composition of each layer in a multilayer structure comprising m layers where m is an integer greater than 1, the method comprising the steps of:
   a) providing an interferometer apparatus with a low-coherence tunable light source;
   b) aligning a portion of the multilayer structure with respect to a measurement region of the interferometer apparatus;
   c) using the interferometer apparatus to observe layers in the multilayer structure, and to measure the optical thickness of each of the observed layers in the multilayer structure as a function of center wavelength of the low-coherence tunable light source;
   d) determining the number of layers m in the multilayer structure by setting m equal to the maximum number of observed layers measured using the low coherence interferometer as a function of center wavelength of the low-coherence tunable light source;
   e) calculating normalized group index of refraction dispersion curves for each of the m layers in the multilayer structure by selecting one center wavelength of the tunable light source as a reference wavelength and calculating the ratio of the measured optical thickness at each measurement wavelength to that measured at the selected reference wavelength for each of the m layers in the multilayer structure; and f) for each of the m layers, identifying the material composition for that layer by comparing its calculated normalized group index of refraction dispersion curve to a reference data base of known materials group index of refraction dispersion curves and finding the best fit material for that layer.

2. The method of claim 1 wherein the same distinct center wavelengths of the low-coherence tunable light source are used to measure every layer in the multilayer structure.

3. The method of claim 1 wherein the reference data base of known materials group index of refraction dispersion curves also includes normalized group index of refraction dispersion curves which are normalized by dividing the group index of refraction dispersion curve by the group index of refraction at the reference wavelength of the incident light source for each of the materials in the reference data base of known materials.

4. The method of claim 1 further comprising the step of determining the physical thickness of each layer in the multilayer structure by dividing its measured optical thickness at each measured center wavelength of the tunable light source by the group index of refraction of the identified material at the respective measured center wavelength and calculating its average for each layer in the multilayer structure.

5. The method of claim 1 where each of the m layers of the multilayer structure is at least partially optically transmissive to light over at least part of the optical spectrum of the low-coherence tunable light source.

6. The method of claim 1 wherein the interferometer apparatus further comprises a variable optical path delay element which is repetitively scanned from a start position to an end position and then from the end position to the start position when repetitively measuring the optical thicknesses of each layer of the m layer multilayer structure, the distance between the start position and the end position being larger than the total optical thickness of the multilayer structure.

7. The method of claim 6 wherein the interferometer apparatus includes a reference interferometer used to accurately track the location of the variable optical path delay element as the variable optical path delay element is repetitively scanned.

8. The method of claim 1 wherein the interferometer apparatus further comprises an optical probe for focusing incident light from the low-coherence tunable light source onto the multilayer structure.

9. The method of claim 8 wherein the optical probe is portable and is coupled to the interferometer apparatus through an optical fiber.

10. The method of claim 9 wherein the portable optical probe is automatically aligned normal to the top surface of the multilayer structure when placed in contact with the top surface of the multilayer structure.

11. The method of claim 1 wherein the low-coherence tunable light source further comprises a supercontinuum light source and a continuously variable wavelength tunable filter.

12. The method of claim 11 wherein the supercontinuum light source emits light over the wavelength range of 400-2400 nm and the variable wavelength tunable filter is continuously tunable between 400-850 nm.

13. The method of claim 1 wherein the multilayer structure is mounted in a measurement cell containing a top optically flat surface located above the top layer of the multilayer structure forming an upper airgap and a bottom optically flat surface located below the bottom layer of the multilayer structure forming a lower airgap during measurements using the interferometer apparatus, the top optically flat surface and the bottom optically flat surface separated by a total airgap, and the optical thickness of the upper airgap and the lower air gap are also measured as a function of wavelength of the low-coherence tunable light source while using the interferometer apparatus to measure the optical thickness of each of the layers in the multilayer structure.

14. The method of claim 13 further comprising the steps of
a) using the interferometer apparatus to measure the optical thickness of the total airgap between the top optical flat surface and the bottom optical flat surface of the measurement cell as a function of wavelength of the low-coherence tunable light source;
b) determining the thickness of the total airgap, the upper airgap, and the lower airgap by dividing their respective measured optical thicknesses at each measured wavelength of the low-coherence tunable light source by the group index of refraction of air at each of the respective wavelengths and calculating the average physical thickness value; and
c) determining the total physical thickness of the multilayer structure by subtracting the average physical thicknesses of the upper airgap and the lower air gap from the total airgap physical thickness.

* * * * *